United States Patent
Crawford et al.

(10) Patent No.: US 6,923,822 B2
(45) Date of Patent: Aug. 2, 2005

(54) BALLOON OCCLUSION DEVICE HAVING A PROXIMAL VALVE

(75) Inventors: Lynn D. Crawford, Irvine, CA (US); Albert Burdulis, Jr., San Francisco, CA (US); Tim Reynolds, Sunnyvale, CA (US); Dan Shumer, San Jose, CA (US); Daryl Edmiston, West Jordan, UT (US); Steve Johnson, West Jordan, UT (US); Karri Schlegel, Salt Lake City, UT (US)

(73) Assignee: Abbott Laboratories, Abbott Park, IL (US)

(*) Notice: Subject to any disclaimer, the term of this patent is extended or adjusted under 35 U.S.C. 154(b) by 587 days.

(21) Appl. No.: 09/882,823

(22) Filed: Jun. 15, 2001

(65) Prior Publication Data

US 2002/0010488 A1 Jan. 24, 2002

Related U.S. Application Data

(60) Provisional application No. 60/212,187, filed on Jun. 16, 2000.

(51) Int. Cl.$^7$ .............................................. A61M 29/00
(52) U.S. Cl. ................... 606/194; 604/96.01; 604/509; 604/264
(58) Field of Search ....................... 606/194; 604/96.01, 604/509, 194, 247, 537, 264, 33

(56) References Cited

U.S. PATENT DOCUMENTS

| 3,467,101 A | 9/1969 | Fogarty et al. |
|---|---|---|
| 4,811,737 A | 3/1989 | Rydell |
| 4,816,020 A | 3/1989 | Brownell |
| 4,846,174 A | 7/1989 | Willard et al. |
| 4,946,466 A | 8/1990 | Pinchuk et al. |
| 5,167,239 A | 12/1992 | Cohen et al. |
| 5,807,330 A | 9/1998 | Teitelbaum |
| 5,833,644 A | 11/1998 | Zadro-Azizi et al. |
| 5,833,650 A | 11/1998 | Imran |
| 5,893,867 A | 4/1999 | Bagaoisan et al. |
| 6,015,402 A | 1/2000 | Sahota |
| 6,022,336 A | 2/2000 | Zadro-Azizi et al. |
| 6,050,972 A | 4/2000 | Zadno-Azizi et al. |
| 6,068,623 A | 5/2000 | Zadno-Azizi et al. |
| 6,102,891 A | 8/2000 | Maria van Erp |
| 6,135,991 A | 10/2000 | Muni et al. |
| 6,190,332 B1 | 2/2001 | Muni et al. |
| 6,217,567 B1 | 4/2001 | Zadno-Azizi et al. |
| 6,228,072 B1 | 5/2001 | Omaleki et al. |
| 6,231,588 B1 | 5/2001 | Zadno-Azizi |
| 6,234,996 B1 | 5/2001 | Bagaoisan et al. |
| 6,252,909 B1 | 6/2001 | Tzannes et al. |
| 6,270,477 B1 | 8/2001 | Bagaoisan et al. |
| 6,273,878 B1 | 8/2001 | Muni |
| 6,325,777 B1 | 12/2001 | Zadno-Azizi et al. |
| 6,325,778 B1 | 12/2001 | Zadno-Azizi et al. |
| 6,355,014 B1 * | 3/2002 | Zadno-Azizi et al. .... 604/99.02 |
| 6,458,096 B1 * | 10/2002 | Briscoe et al. ........... 604/96.01 |

FOREIGN PATENT DOCUMENTS

| GB | 2080493 A * | 3/1982 | ............. F16K/3/26 |
|---|---|---|---|
| WO | WO 88/00844 | 2/1988 | |
| WO | WO 99/42161 | 8/1999 | |

* cited by examiner

*Primary Examiner*—Henry Bennett
*Assistant Examiner*—Andrea M. Ragonese

(57) ABSTRACT

A medical device for vessel occlusion, the medical device including an elongated body having a distal end portion, a proximal end portion, and a lumen disposed therethrough, an balloon disposed at the distal end portion of the elongated body, the balloon in fluid communication with the lumen. An opening defined at the proximal end portion of the elongated body, the opening being in fluid communication with the balloon via the lumen, and a valve body moveably disposed at the proximal end portion of the elongated body, the valve body movable between a closed position and an open position, the valve body configured to engage a surface of the elongated body, distal to the opening, to seal the opening when the valve body is in the closed position.

19 Claims, 15 Drawing Sheets

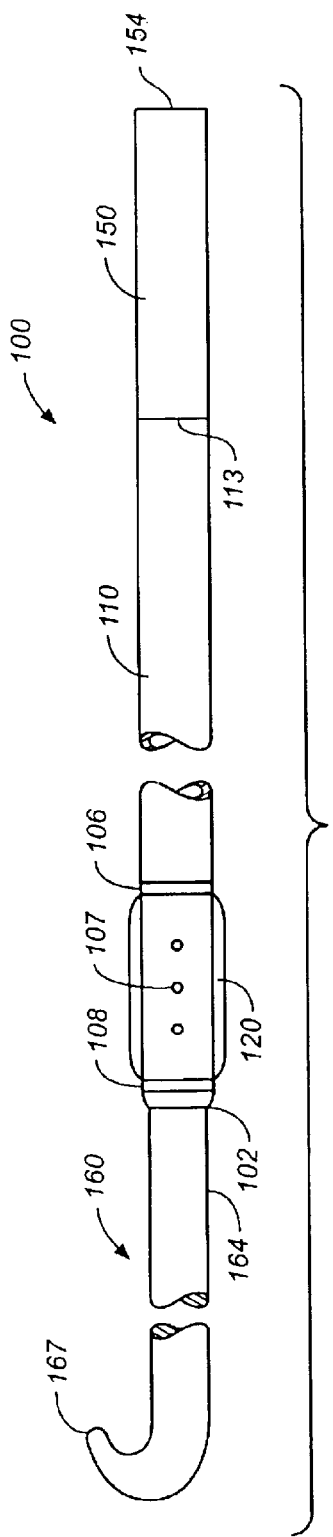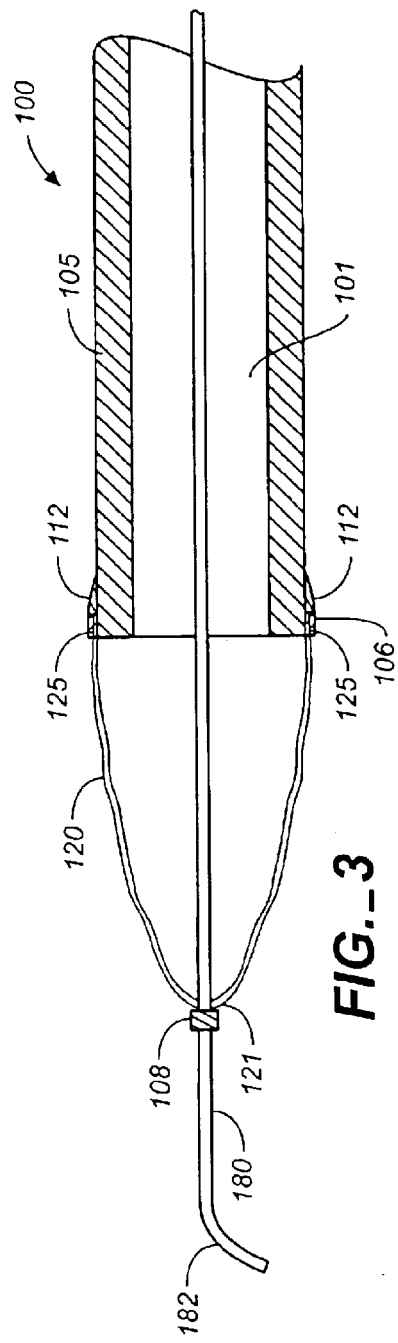
FIG._1
FIG._3

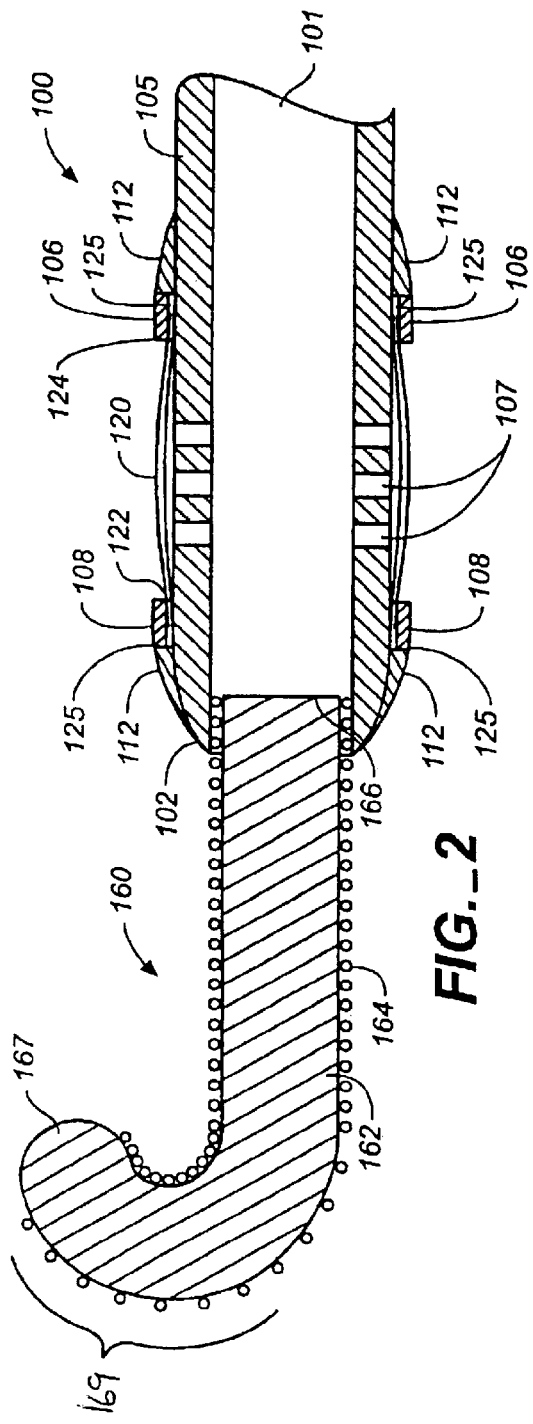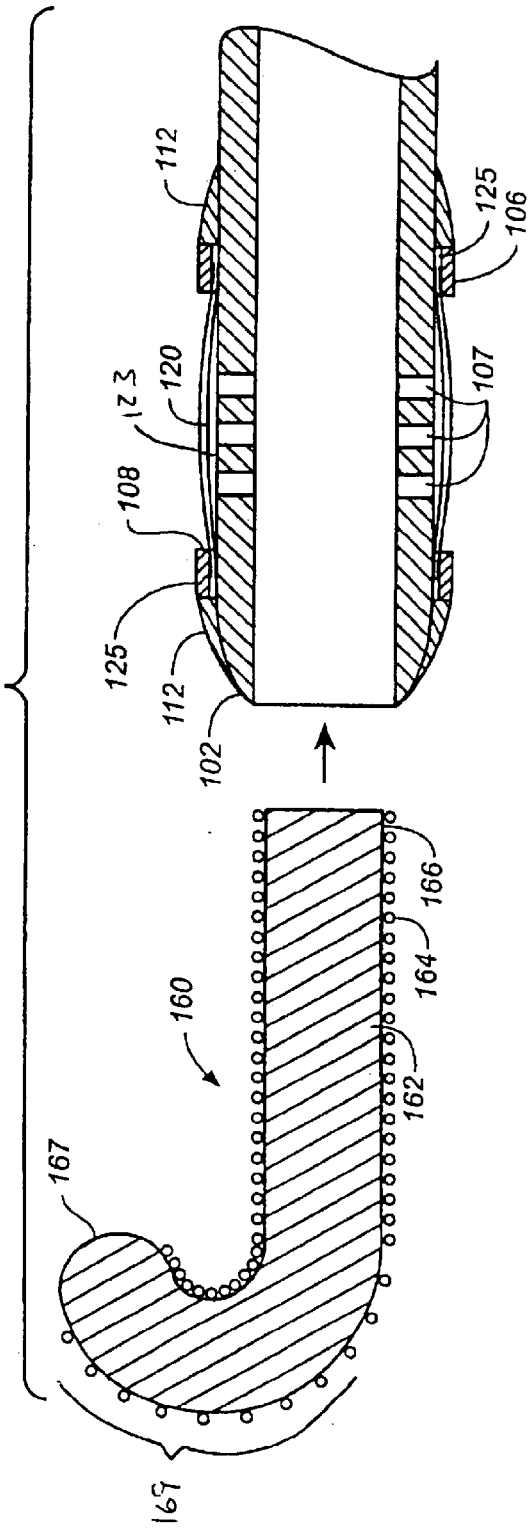

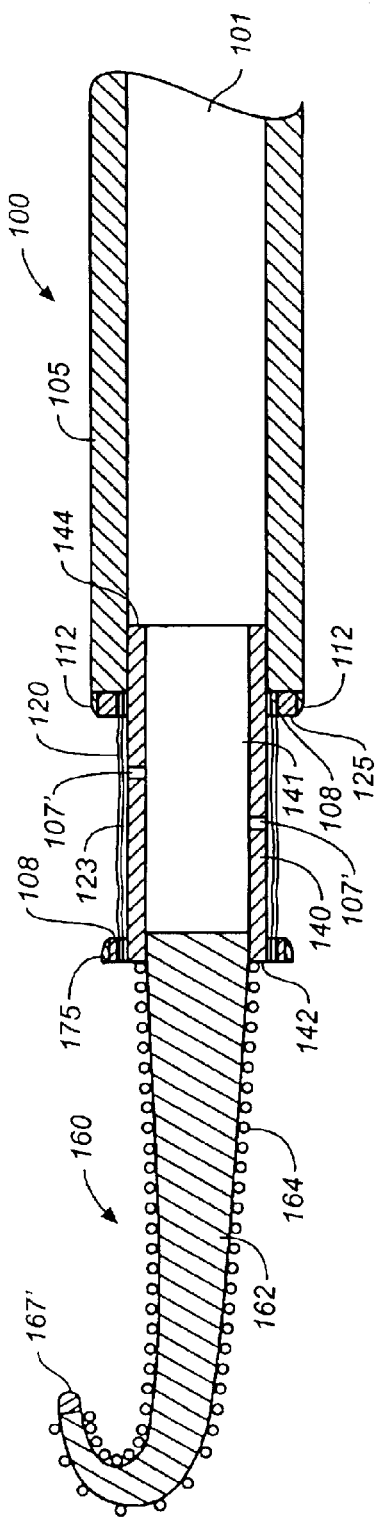
FIG._4
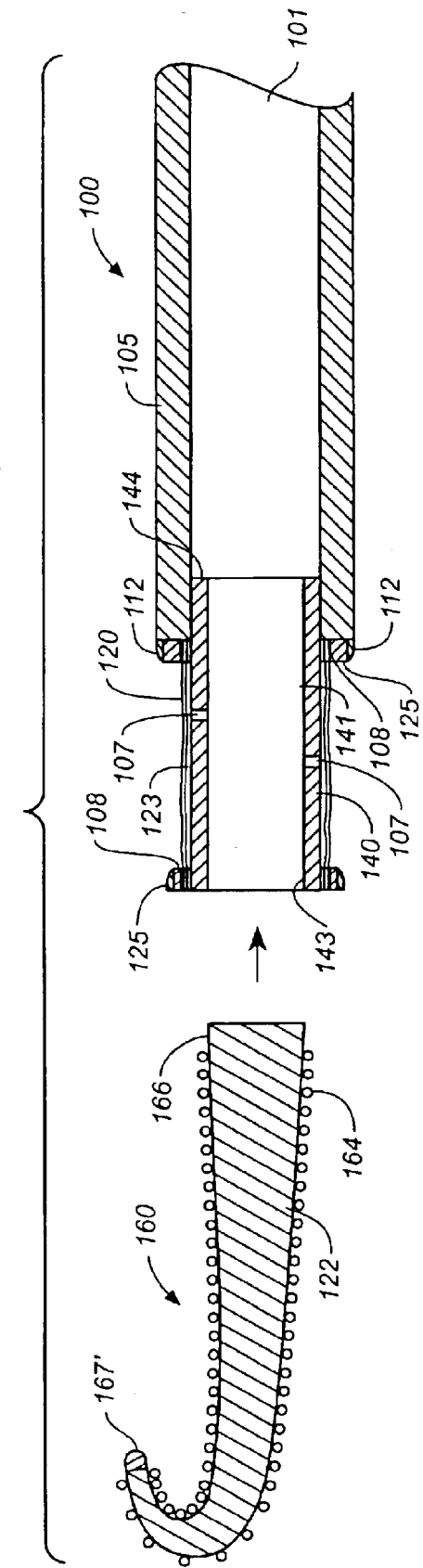
FIG._5

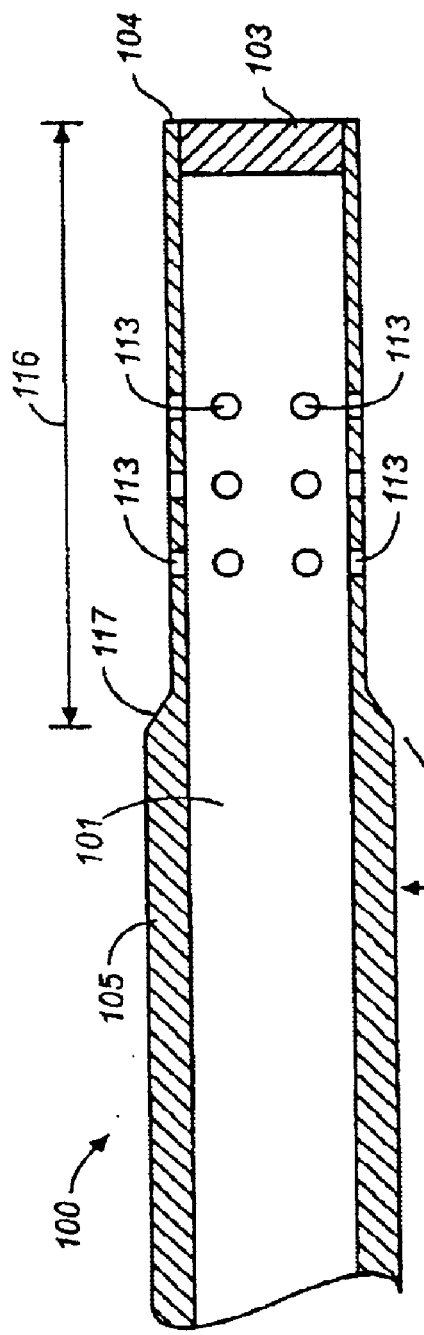
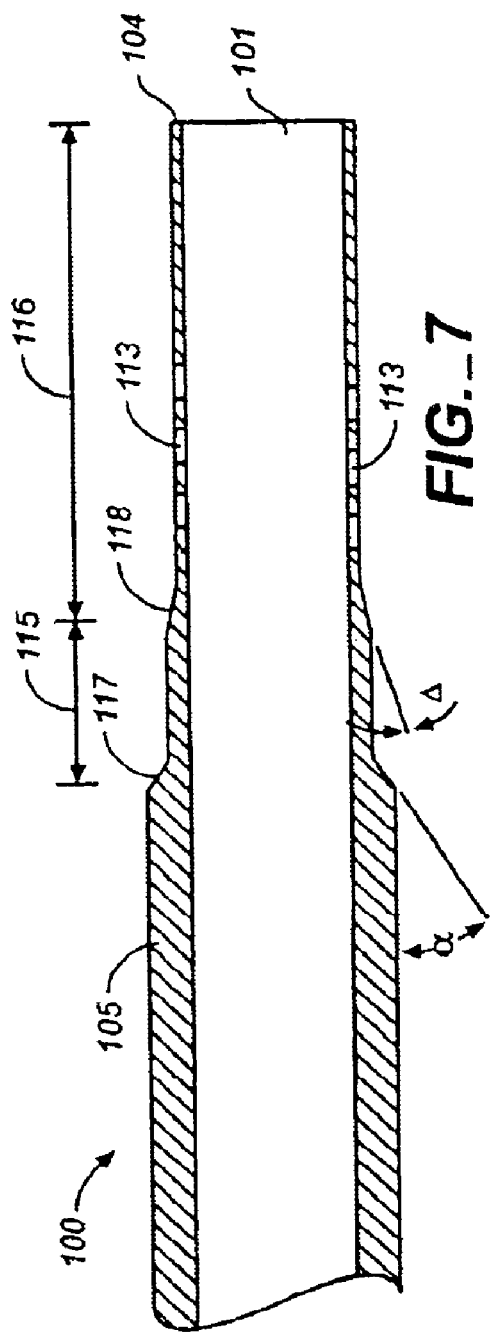

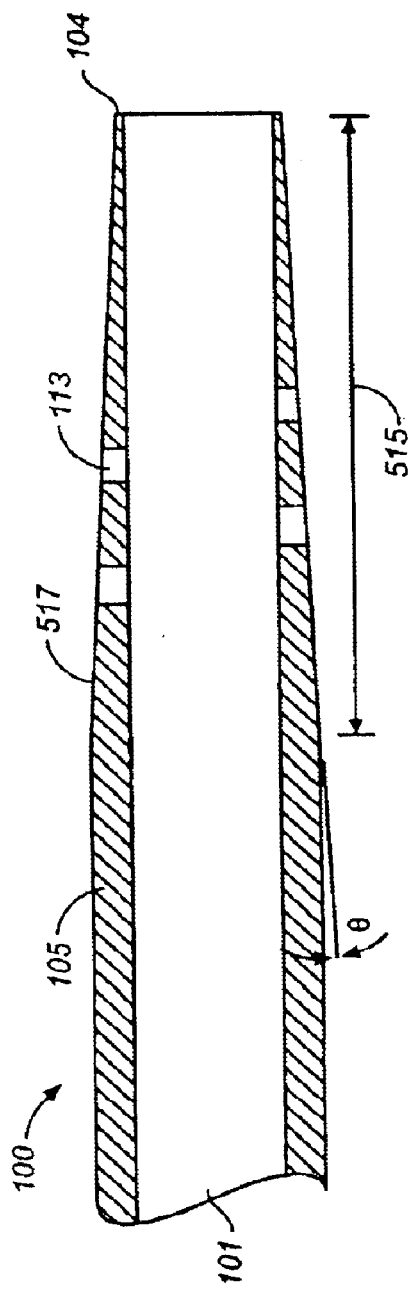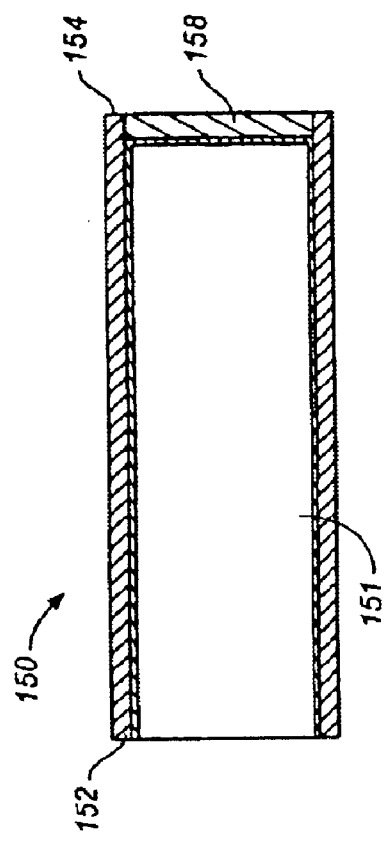

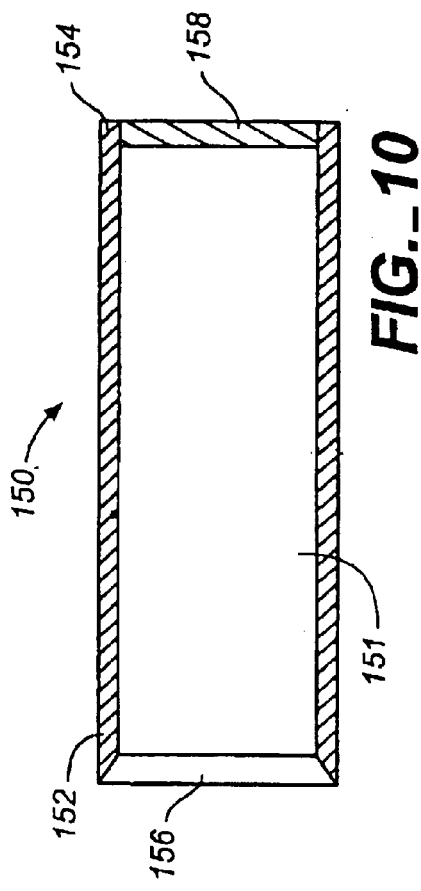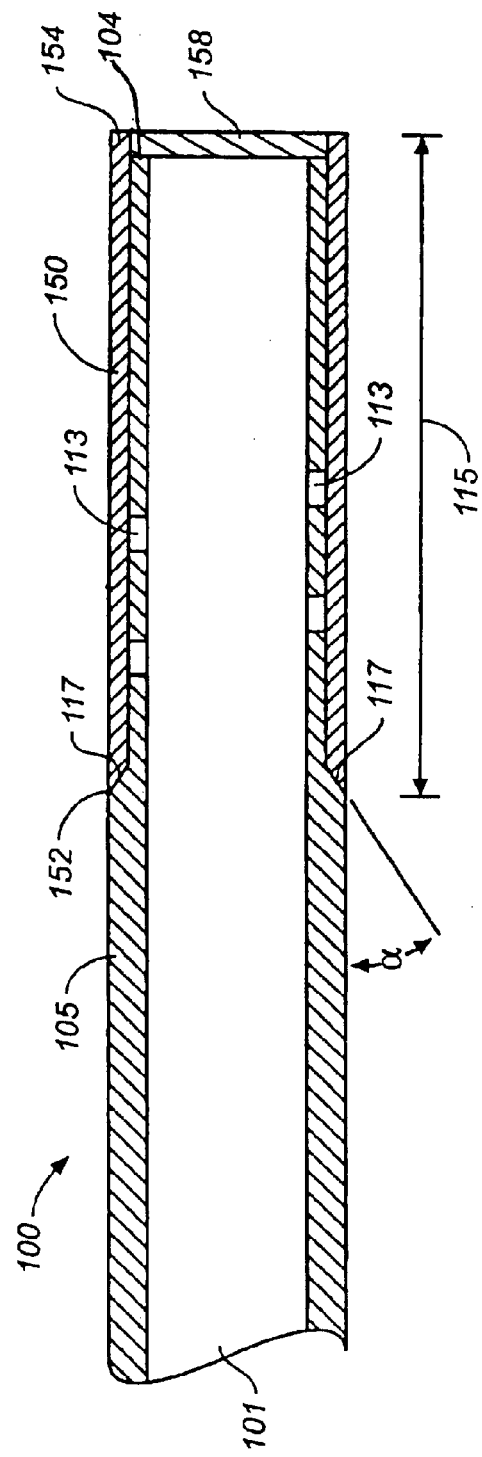

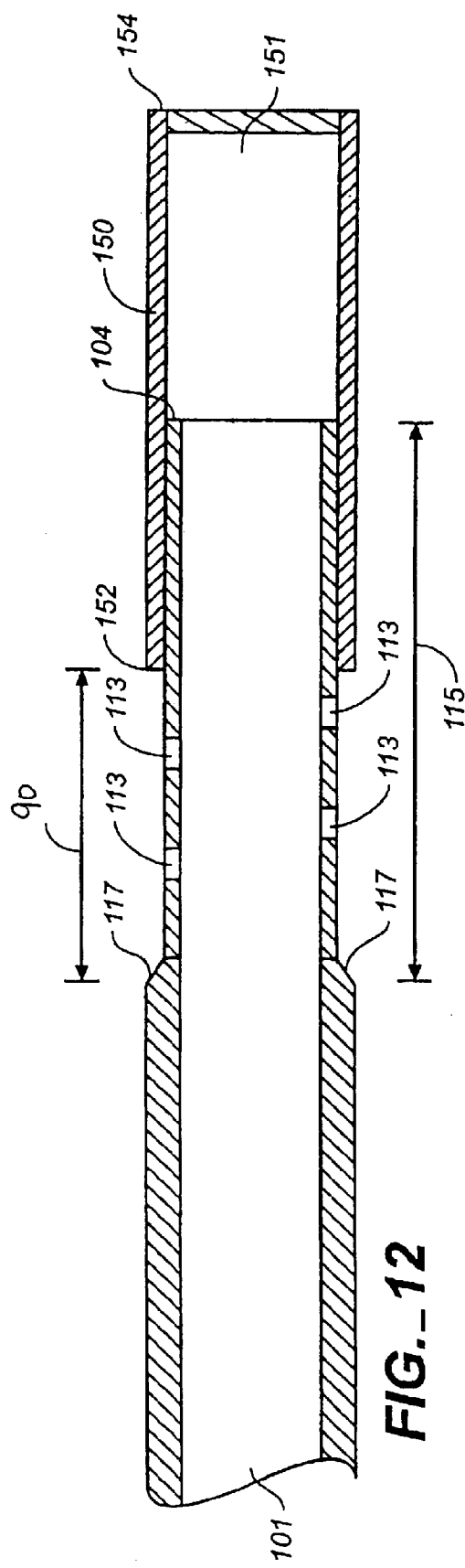
FIG._12
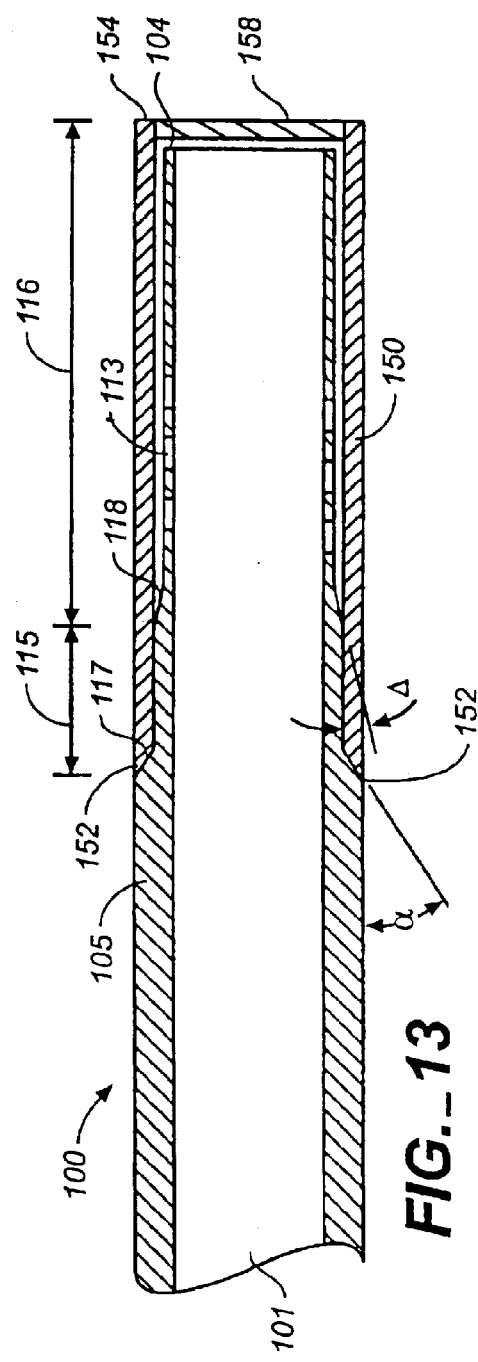
FIG._13

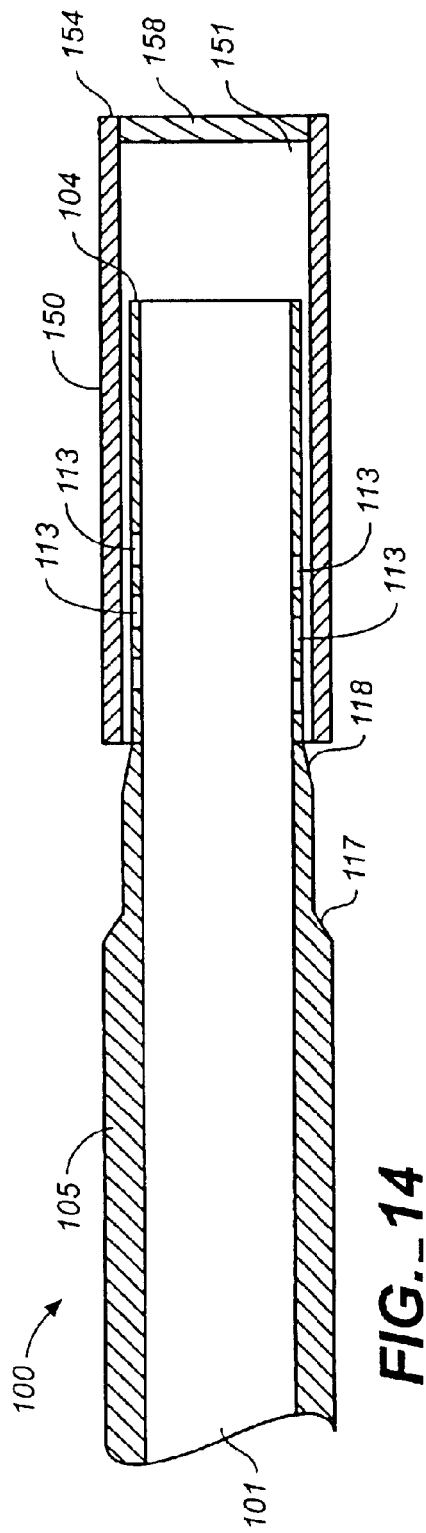
FIG._14
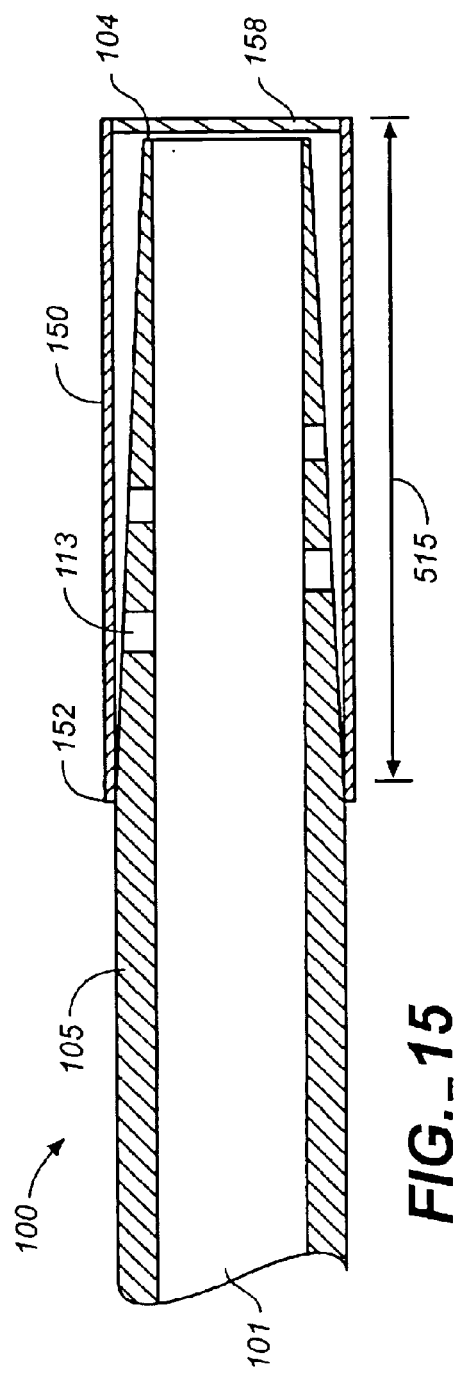
FIG._15

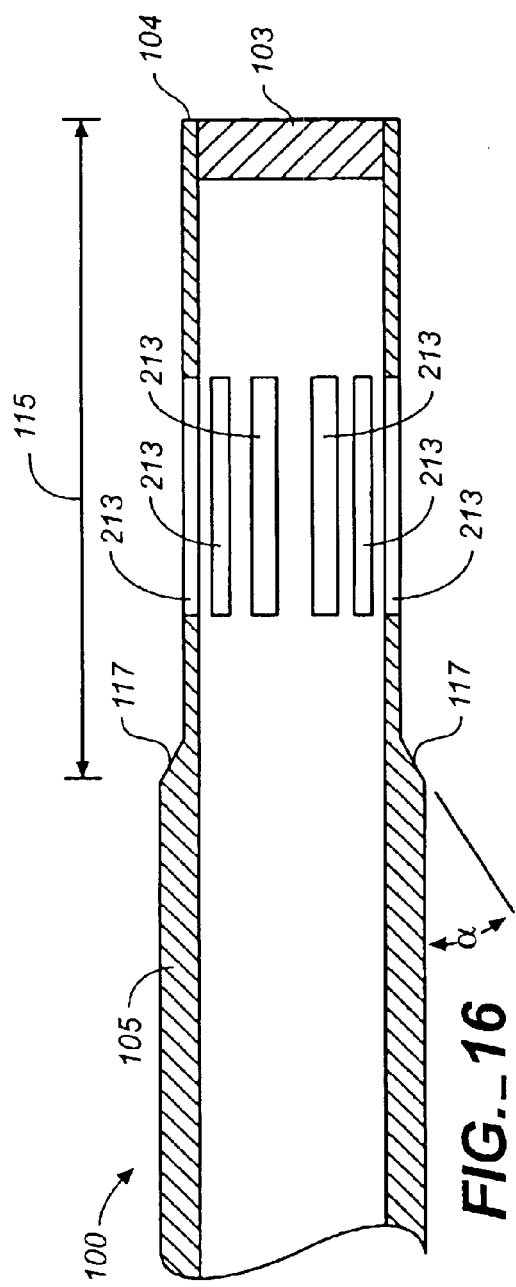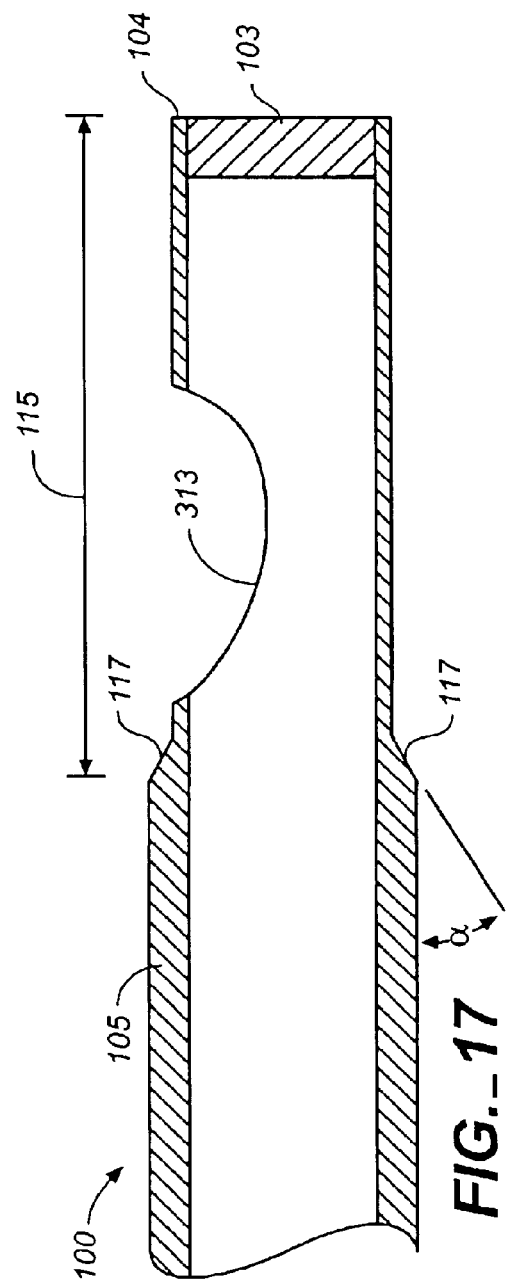

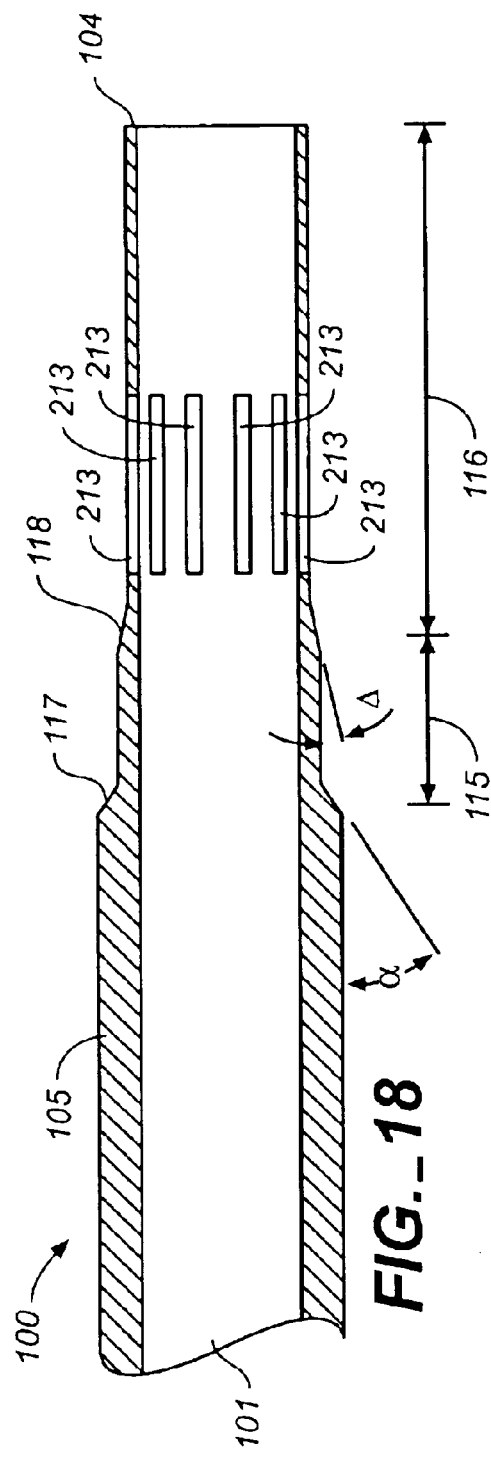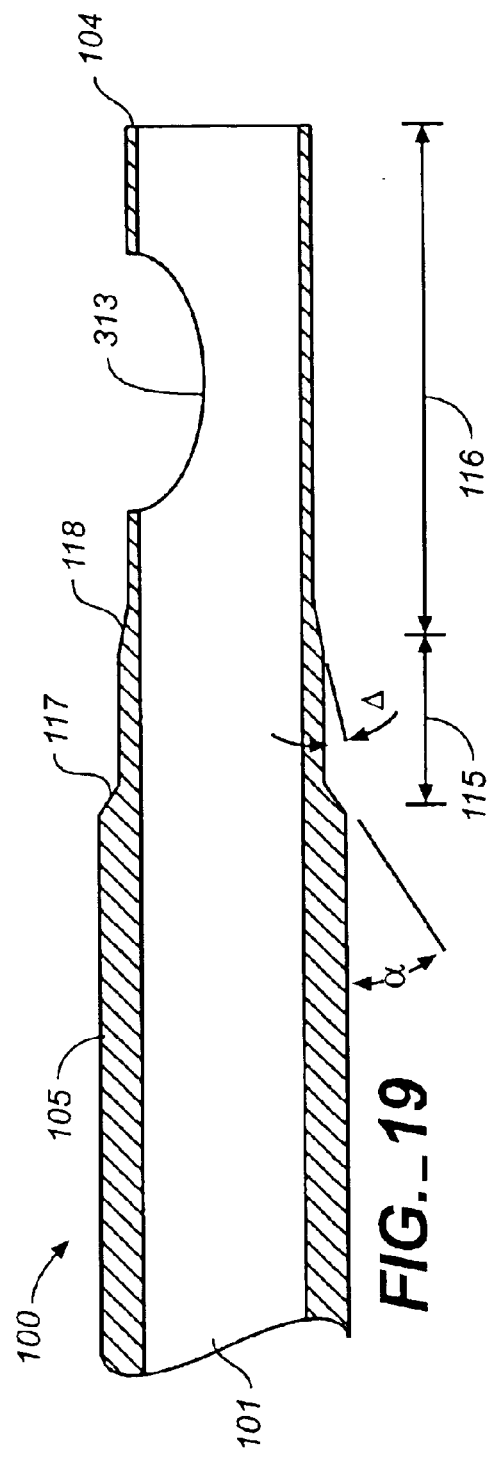

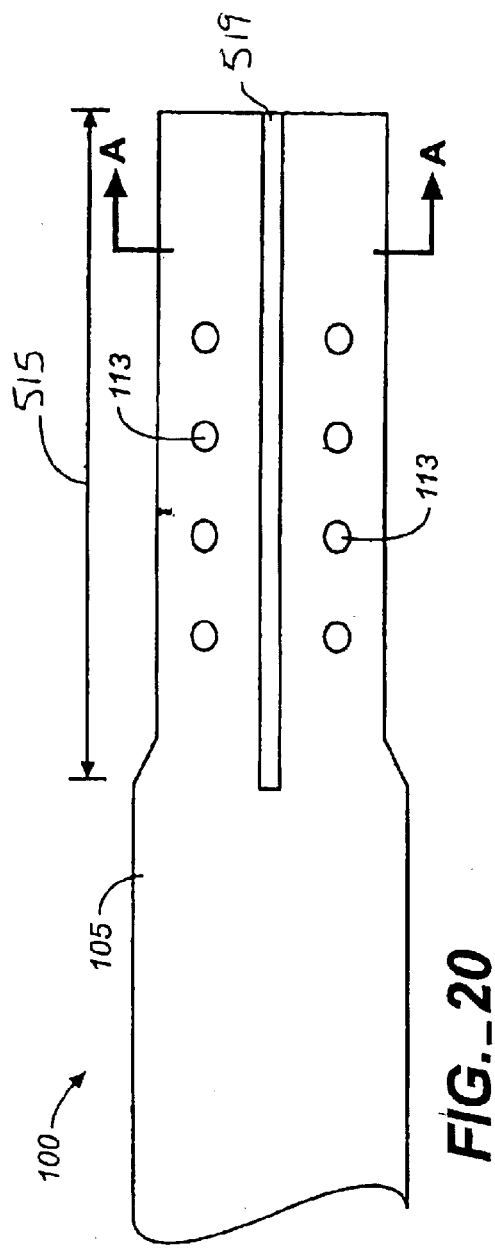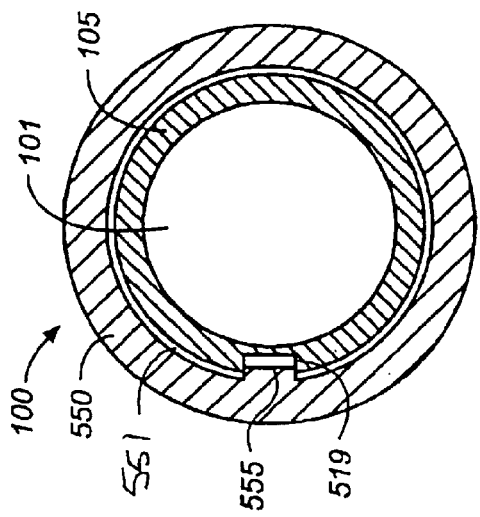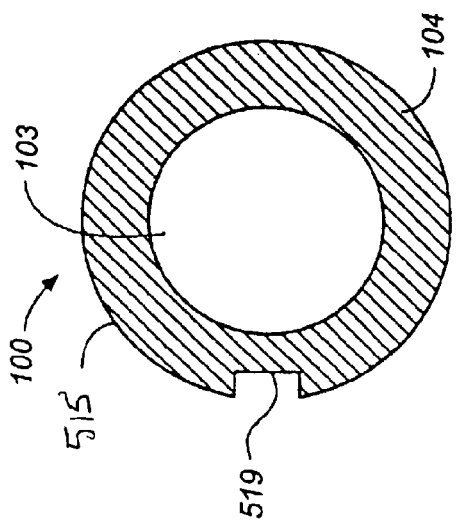

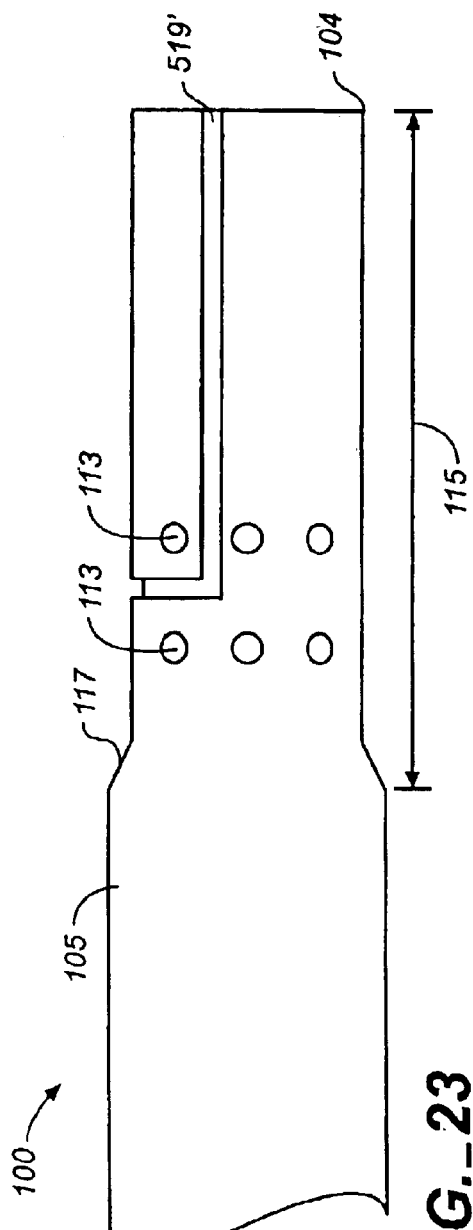
FIG._23
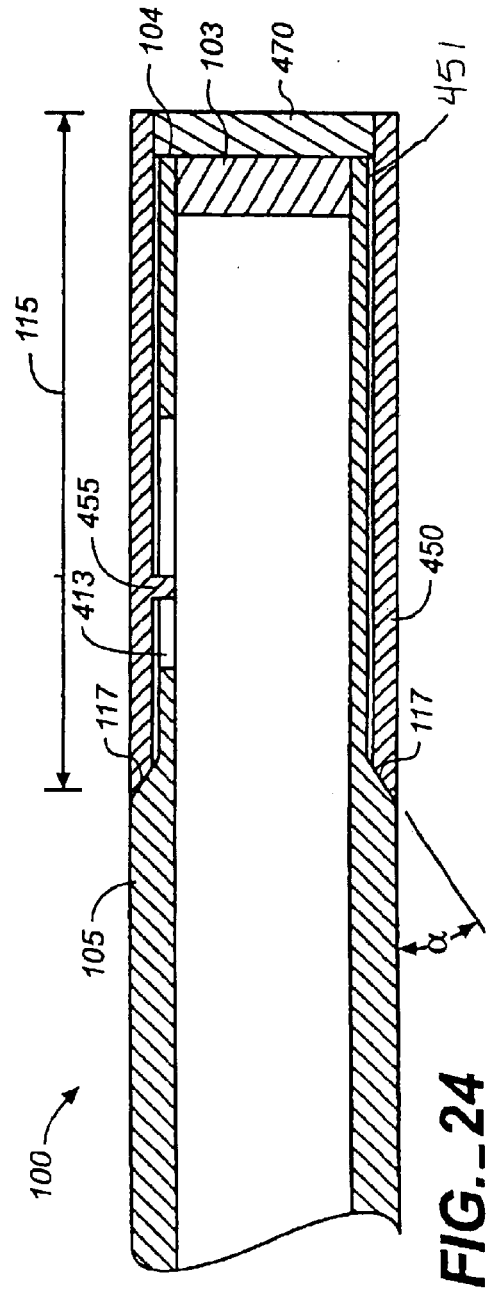
FIG._24

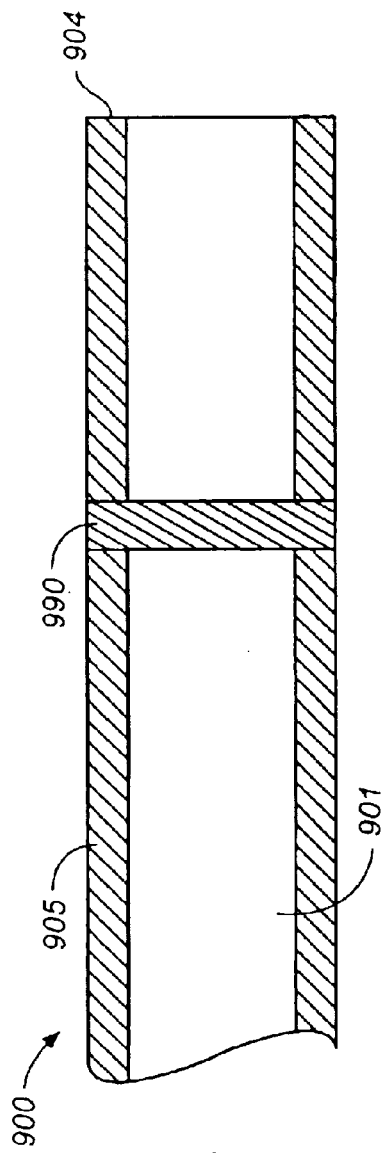
FIG._25
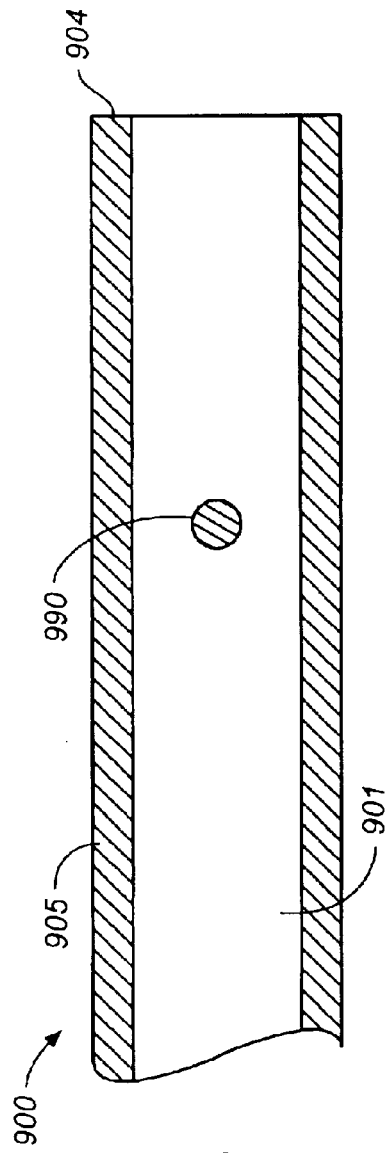
FIG._26
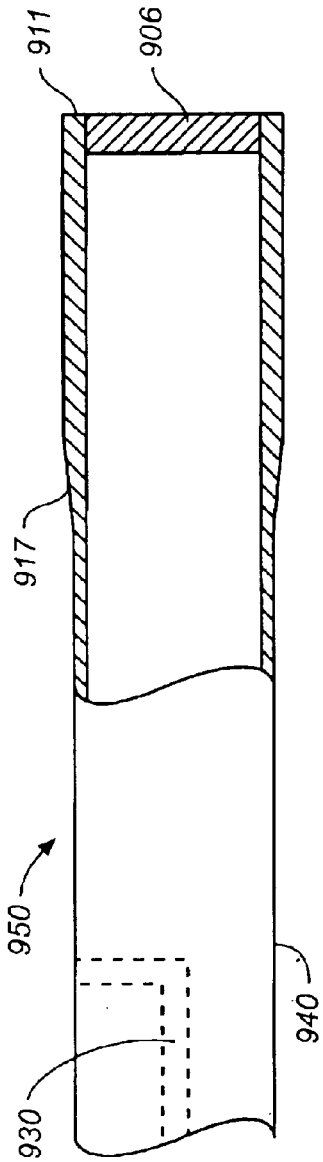
FIG._27

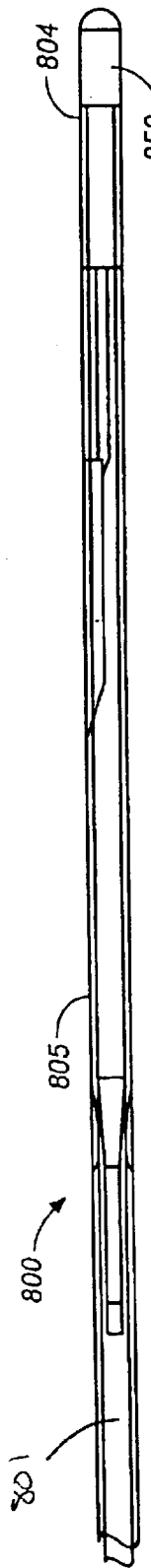
FIG._28
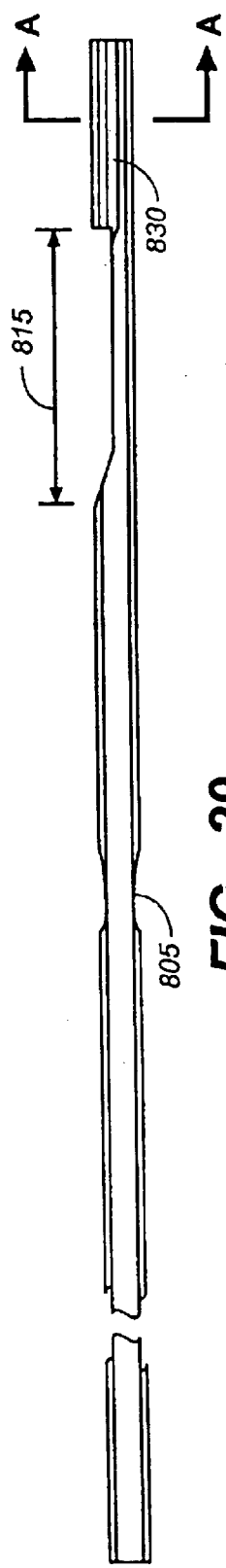
FIG._29
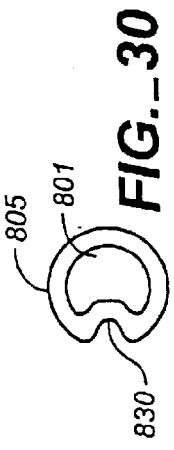
FIG._30
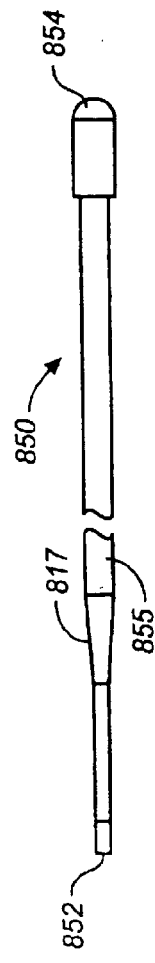
FIG._31
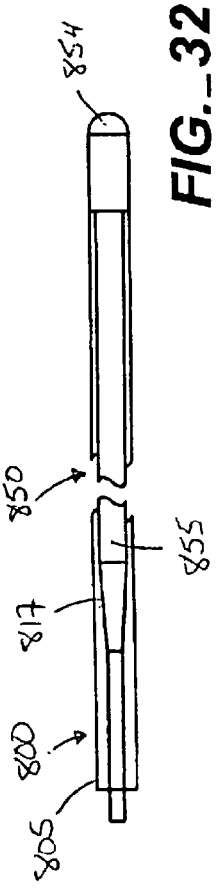
FIG._32

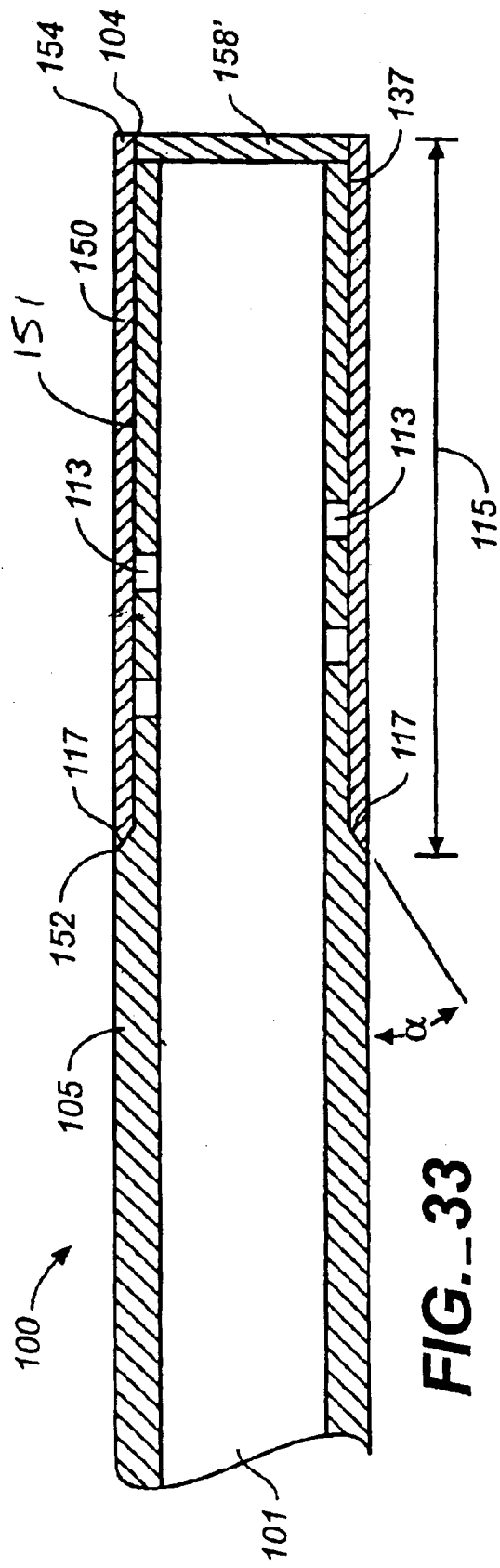

BALLOON OCCLUSION DEVICE HAVING A PROXIMAL VALVE

CLAIM OF PRIORITY

The present application claims priority under 35 U.S.C. § 119 to U.S. Provisional Application Ser. No. 60/212,187 filed on Jun. 16, 2000, entitled "Angioplasty Catheter", the entirety of which is incorporated by reference herewith.

1. FIELD OF THE INVENTION

The present invention relates to medical devices, specifically a medical device having a low profile valve for selectively inflating and deflating an inflatable balloon disposed upon the medical device, wherein the valve allows passage of interventional devices over the medical device during use.

2. BACKGROUND OF THE INVENTION

In order to perform many vascular procedures a guidewire is initially inserted into the patient's vasculature. The guidewire is generally inserted into the patient through an incision created in the patient's femoral artery. After the guidewire has been placed within the patient's vasculature, other interventional devices, such as catheters, maybe be passed over the guidewire. As used herein, the term "interventional device" is intended to include, but not be limited to, any known devices capable of being inserted within the human vasculature for diagnosis, treatment or inspection thereof. Additionally the terms "catheter" and "guidewire" as utilized herein are intended to be interchangeable when referring to the medical device in accordance with the present invention.

One difficulty associated with this procedure however is that the guidewire must be held in place while the interventional device is passed over the guidewire. It is possible that the guidewire may become dislodged from the position where it was initially placed, therefore when a interventional device is advanced over the guidewire it may not be advanced to the desired position.

A common medical procedure where it is desirable to place a guidewire and then advance interventional devices over the guidewire are angioplasty and/or bypass procedures. In an angioplasty procedure, the guidewire may be advanced up to or through a blockage in a patient's vessel, wherein a catheter containing a stent or other interventional device is then passed over the guidewire to the occluded area.

A common procedure performed on occluded or narrowed vessels is to place an angioplasty catheter having a balloon disposed on one end within the occluded region and expanding the balloon, thereby expanding the vessel. The balloon catheter is typically formed of a flexible material wherein the catheter includes radiopaque markings thereon in order to properly place the balloon within the desired region. The balloon catheter is placed within the patient's vasculature through a percutaneous access site such as the femoral artery. The balloon catheter is placed within the patient's vasculature by tracking the catheter over a guidewire which has been placed first. The guidewire enables a user to more easily track the flexible catheter into a proper position, wherein the balloon may be inflated to expand the vessel and/or occlusion therein.

Another commonly utilized cardiovascular procedure is stenting. Stenting is a procedure wherein a expanding device is placed within an obstructed vessel in order to hold open or expand the constricted vessel. Stenting procedures are carried out in a manner similar to the balloon angioplasty procedure described above. Many times both procedures will be performed wherein the vessel may be first expanded with a balloon catheter and subsequently a stent will be deployed thereafter to maintain the expanded diameter of the vessel.

During stenting and/or balloon angioplasty procedures there is the risk that plaque or other debris may be dislodged from the inner walls of the vessel. The plaque may be in the form of small particles which may be carried within the patient's blood stream and may lead to other complications such as embolism if the particles become lodged into a branch vessel or artery and restrict or prevent blood flow to that vessel or artery.

Therefore it is desirable to provide a device which may be utilized during a medical procedure such as those described above wherein the device may be utilized to prevent dislodged particles from flowing into a patient's blood stream and potentially causing further blockage or a stroke. It is also desirable to provide a device which may be utilized to temporarily occlude a vessel distal an area where a surgical procedure is to be performed thereby providing a contained area for the surgeon to operate within.

One such device has been disclosed in U.S. Pat. No. 5,807,330 to Teitelbaum, the entirety of which is incorporated by reference herewith. However, there remains a desire for an improved low profile valve for the device of Teitelbaum.

A further object of the present invention therefore is to provide a medical device having a low profile valve means disposed on the proximal end portion, wherein the valve may be selectively opened and closed thereby enabling the inflation and deflation of a balloon disposed at the distal end portion of the device. Furthermore, the valve provides a sufficiently low profile area wherein other interventional devices may be passed over the medical device to conduct surgical procedures within the patient's vasculature.

A further object of the present invention is to provide a medical device wherein balloon disposed upon the distal end portion of the device may be selectively inflated or deflated through a valve means wherein the inflation device is removable from the valve means.

SUMMARY OF THE INVENTION

In one aspect of the invention there is provided a medical device for vessel occlusion, the medical device including an elongated body having a distal end portion, a proximal end portion, and a lumen disposed therethrough. The medical device further includes an inflatable balloon disposed at the distal end portion of the elongated body, the balloon being in fluid communication with the lumen, and an opening defined at the proximal end portion of the elongated body, the opening being in fluid communication with the balloon via the lumen. A valve body is moveably disposed at the proximal end portion of the elongated body; the valve body being movable between a closed position and an open position. The valve body is configured to engage a surface of the elongated body, distal to the opening, to seal the opening when the valve body is in the closed position.

In another aspect of the invention, there is provided a medical device for vessel occlusion. The medical device includes an elongated body having a distal end portion, a proximal end portion, and a lumen disposed therethrough. The medical device further includes an inflatable balloon disposed at the distal end portion of the elongated body, the balloon being in fluid communication with the lumen. An opening is defined at the proximal end portion of the elongated body, the opening being in fluid communication with the balloon via the lumen. A valve body is moveably disposed at the proximal end portion of the elongated body, the valve body being movable between a closed position and an open position. The valve body is configured to engage an outer surface of the elongated body to seal the opening when the valve body is in the closed position.

In another aspect of the present invention there is provided a medical device for vessel occlusion, the medical device including an elongated body having a distal end portion, a proximal end portion, and a lumen disposed therethrough. The medical device further includes an inflatable balloon disposed at the distal end portion of the elongated body, the inflatable balloon being in fluid communication with the lumen. An opening is defined at the proximal end portion of the elongated body, the opening being in fluid communication with the balloon via the lumen. A valve body is moveably disposed at the proximal end portion of the elongated body, the valve body being movable between a closed position and an open position. The valve body is configured to engage an outer surface at the proximal end portion of the elongated body, distal to the opening, to seal the opening when the valve body is in the closed position. The valve body includes a side wall having a cavity defined therein to receive the proximal end portion of the elongated body, and an outer surface substantially flush with an outer surface of the distal end portion of the elongated body when in the closed position. At least one of the valve body and the elongated body has a projection extending therefrom for mating engagement with the other body to prevent inadvertent movement of the valve body at least when in the closed position.

DETAILED DESCRIPTION OF THE DRAWINGS

The objects and advantages of the invention will become apparent from the following detailed description of preferred embodiments thereof in connection with the accompanying drawings in which like numerals designate like elements and in which:

FIG. 1 is a side view of the medical device according to the present invention;

FIG. 2 is a partial cross-sectional side view of one representative embodiment of the distal tip of the medical device according to the present invention;

FIG. 2B is a partial cross-sectional side view of one representative embodiment of a removable distal tip according to the present invention;

FIG. 3 is a partial cross-sectional side view of another representative embodiment of the distal tip of the medical device according to the present invention;

FIG. 4 is a partial cross-sectional side view of another representative embodiment of the distal tip of the medical device according to the present invention;

FIG. 5 is a partial cross-sectional side view of still another representative embodiment of the distal tip of the medical device according to the present invention;

FIG. 6 is a partial cross-sectional side view of one representative embodiment of the proximal end portion of the medical device according to the present invention;

FIG. 7 is a partial cross-sectional side view of another representative embodiment of the proximal end portion of the medical device according to the present invention;

FIG. 8 is a partial cross-sectional side view of another representative alternative embodiment of the proximal end portion of the medical device according to the present invention;

FIG. 9 is a cross-sectional side view of a representative embodiment of a valve body according to the present invention;

FIG. 10 is a cross-sectional side view of a representative alternative embodiment of the valve body according to the present invention;

FIG. 11 is a partial cross-sectional side view of a representative embodiment of the proximal end portion of the medical device according to the present invention illustrating the valve body disposed thereabout;

FIG. 12 is a partial cross-sectional side view of the proximal end portion of the medical device according to the present invention showing the valve body in an opened position;

FIG. 13 is a partial cross-sectional side view of an alternative representative embodiment of the proximal end portion of the medical device according to the present invention illustrating the valve body disposed thereabout;

FIG. 14 is a partial cross-sectional side view of the alternative embodiment of the proximal end portion of the medical device according to the present invention showing the valve body in an opened position;

FIG. 15 is a partial cross-sectional side view of another alternative embodiment of the proximal end portion of the medical device according to the present invention illustrating the valve body disposed thereabout;

FIG. 16 is a partial cross-sectional side view of of the proximal end portion illustrating a plurality of apertures formed within the wall of the medical device;

FIG. 17 is a partial cross-sectional side view of of the proximal end portion illustrating a skive formed within the wall of the medical device;

FIG. 18 is a partial cross-sectional side view of an alternative embodiment of the proximal end portion of the medical device according to the present invention illustrating a plurality of elongated slots formed within the wall of the medical device;

FIG. 19 is a partial cross-sectional side view of the alternative embodiment of the proximal end of the medical device according to the present invention illustrating a skive formed within the proximal end portion of the medical device;

FIG. 20 is a partial side view of a representative alternative embodiment of the proximal end of the medical device according to the present invention;

FIG. 21 is a cross-sectional end view of the alternative embodiment of the proximal end portion of the medical device shown in FIG. 20;

FIG. 22 is a cross-sectional end view of the alternative embodiment of the proximal end portion of the medical device shown in FIG. 20;

FIG. 23 is a partial side view of another representative alternative embodiment of the proximal end portion of the medical device according to the present invention;

FIG. 24 is a partial cross-sectional side view of another representative alternative embodiment of the proximal end portion of the medical device according to the present invention;

FIG. 25 is a partial cross-sectional side view of another representative alternative embodiment of the proximal end portion of the medical device according to the present invention;

FIG. 26 is a partial cross-sectional top view of another representative alternative embodiment of the proximal end portion of the medical device according to the present invention;

FIG. 27 is a partial cross-sectional side view an alternative embodiment of the valve body of the medical device according to the present invention;

FIG. 28 is a partial cross-sectional top view of an alternative embodiment of the medical device according to the present invention;

FIG. 29 is a partial cross-sectional side view of the alternative embodiment of the medical device as shown in FIG. 28;

FIG. 30 is a cross-sectional end view taken about line A—A of FIG. 29, of the alternative embodiment of the medical device of FIG. 29;

FIG. 31 is a partial side view of the valve body according to FIG. 28;

FIG. 32 is a partial cross-sectional side view of the valve body of FIG. 31 as disposed within the proximal end portion of the medical device of FIG. 28; and FIG. 33 is a partial cross-sectional side view of an alternative embodiment of the proximal end portion and valve body in accordance with the present invention.

DETAILED DESCRIPTION OF A PREFERRED EMBODIMENT

In accordance with the present invention there is shown and described a medical device for vessel occlusion. The medical device includes an elongated body having a distal end portion, a proximal end portion, and a lumen disposed therethrough. A balloon is disposed at the distal end portion of the elongated body, the balloon being in fluid communication with the lumen. An opening is defined at the proximal end portion of the elongated body, the opening being in fluid communication with the balloon via the lumen. A valve is disposed at the proximal end portion of the elongated body, the valve including a valve body movable between a closed position and an open position. The valve body is configured to engage a surface of the elongated body, distal to the opening, to seal the opening when the valve body is in the closed position.

Referring now to FIGS. 1, 2, and 11, there is shown a representative embodiment of a medical device 100 according to the present invention. The medical device 100 includes an elongated body 105 having a proximal end portion 104 and a distal end portion 102 and at least one lumen 101 disposed therethrough defining an inner cavity. An inflatable balloon 120 is disposed proximate the distal end portion 102, wherein the inner cavity of the balloon 120 is in fluid communication with the lumen 101 of the medical device 100.

If desired, at least one radiopaque marker 108 may be disposed at the distal end portion of the elongated body 105 proximate the balloon 120. Preferably, at least one radiopaque marker 108 is disposed within the distal end of the cavity defined by the balloon, and if desired, at least one proximal radiopaque marker 106 is disposed within the proximal end of the cavity defined by the balloon. The medical device 100 also may include a flexible tip 160. The flexible tip 160 may extend from the distal end portion 102 of the medical device 100.

In accordance with the present invention, the medical device 100 includes at its proximal end portion 104 a valve body 150, wherein the valve body 150 is movable between a closed position and an open position; the valve body configured to engage a surface of the elongated body to seal the opening when the valve body is in the closed position. The medical device 100 will be described in greater detail below.

The elongated body 105 of the medical device 100 may be constructed of any suitable material including but not limited to polymide material, alloy materials, and metallic materials such as stainless steel hypodermic tubing which is available from MicroGroup® Inc., Medway, Md. Preferably the elongated body 105 of the medical device 100 is constructed of a nickel titanium alloy known as Nitinol. Materials such as these are available from various suppliers such as Memry Corp., Menlo Park, Calif. U.S. The above materials should not be considered limiting in any manner, it is contemplated that the elongated body 105 may be constructed of any bio-compatible material. For example, the elongated body may be constructed of a polymer such as polymide tubing from HV Technologies, Inc. of Trenton, Ga. U.S. The elongated body 105 may be manufactured using well known techniques such as swaging, machining, grinding, electropolishing, EDM, heat forming, extruding, or by any other processes commonly used to shape and configure small metal or polymer components. Additionally, the elongated body 105 may be constructed from polypropylene or urethane by an extrusion process using an extruder such as that available from Medical Extrusion Technologies, Inc. Murieta, Calif. U.S.

The elongated body 105 may be further coated with any of a variety of materials to enhance performance if desired. For example possible coating materials include lubricious materials such as Teflon® available from DuPont De Nemours, Wilmington, Del. U.S., and hydrophobic materials such as silicone lubricant dispersion PN 4097, available from Applied Silicone Corp., Ventura, Calif. U.S., or a hydrophilic materials such as hydrogel available from Hydromer, Branchburg, N.J. U.S., or lubricious coatings such as those available from Hydro-Silk of Merritt Island, Fla., under the trade name TUA Systems.

The elongated body 105 may have any suitable cross-sectional shape, including elliptical, polygon, or prismatic, although a circular cross-section generally is preferred. The cross-sectional dimension generally is between about 0.01 millimeters to about 1.0 millimeters, preferably between about 0.10 millimeters and about 0.50 millimeters, most preferably between about 0.250 millimeters and about 0.450 millimeters. Furthermore the medical device 100 may have an overall length between about 180 centimeters and 400 centimeters, preferably between about 250 centimeters and about 350 centimeters, more preferably the medical device has a length between about 290 centimeters and about 310 centimeters, and most preferably about 300 centimeters.

Referring now to FIG. 2 there is shown a partial cross-sectional side view of the distal end portion 102 of the medical device 100. As shown in FIG. 2, a flexible tip 160 may extend from the distal end portion 102 of the elongated body 105. A variety of distal tip configurations are known and used in the art, each generally capable of performing particular functions. For example, and as embodied herein, the flexible tip 160 is constructed of a solid inner core wire 162 of type 304 stainless steel, wherein the solid core 162 is wrapped with a bio-compatible wire 164. Examples of a bio-compatible wire 164 which maybe utilized include stainless steel, Nitinol, Titanium, Platinum, Iridium, and similar bio-compatible materials. In a preferred embodiment the bio-compatible wire 164 is a platinum wire. Platinum wire is preferably used because platinum wire is visible under fluoroscopy thereby enabling a surgeon to locate the flexible tip 160 within a patient's body in use. The pre-formed curve 169, in addition to a blunt tip 167 form, includes an-atramatic tip thereby allowing the medical device 100 to be inserted within a patient's vasculature. The pre-formed curve 169 ensures that the blunt tip 167 does not pierce the vessel/artery or organ through which the medical device 100 is being advanced. It shall be understood that the pre-formed curve 169 remains sufficiently pliable and elastic whereby an interventional device may be advanced over the outer diameter of the medical device 100 such that the pre-formed curve 169 will straighten and all the medical device to pass over. Such tip designs are well known in the art.

As shown in FIG. 2, the proximal end 166 of the flexible tip 160 as embodied herein is adapted to be received within the lumen 101 of the medical device 100. The proximal end 166 of the flexible tip 160 may be secured within the lumen 101 through the use of a bio-compatible adhesive, such as Locktite® 4014, or through mechanical fastening methods such as soldering or a friction fit. In a preferred embodiment, the distal end portion 102 of the elongated body 105 is deformed about the diameter of the distal end 166 of the flexible tip 160, thereby forming a fluid tight seal between the lumen 101 and the flexible tip 160.

In accordance with another embodiment of the invention, referring now to FIG. 2B there is shown an alternative embodiment of the flexible tip 160 as described above. As shown in FIG. 2B, the flexible tip 160 may be constructed in the same or similar manner as that described above, wherein like reference numerals have been utilized to denote similar features. The flexible tip 160 of FIG. 2B further includes a proximal end 166, wherein the proximal end 166 is adapted to be detachably received within the lumen 101 of the elongated body 105. In use, it is desirable to pre-prime the medical device 100, that is to remove as much air as possible from the lumen 101 as well as the chamber 123 defined by the balloon 120. Typically this is done by drawing a vacuum within the lumen 101 and chamber 123 and allowing a bio-compatible fluid such as saline or contrast to fill the lumen 101 and chamber 123 of the medical device 100. Although most air is removed from the system, removal of 100% of the air typically may not be possible. By constructing the medical device 100 with a removable tip as shown in FIGS. 2B and 4, a bio-compatible fluid may be flushed distally through the lumen 101 and the chamber 123 thereby forcing air out of these spaces. After the air has been forced through the medical device 100, the flexible tip 160 is attached to the distal end portion 102 of the elongated body 105, wherein the medical device 100 is ready for use.

As previously noted, an inflatable balloon is provided at the distal end portion of the medical device of the present invention. The balloon 120 may be constructed of any suitable, flexible bio-compatible materials depending upon the intended function of the medical device 100. The balloon may be inelastic, if desired, although generally elastic materials are preferred. Examples of materials of which the balloon 120 may be formed are urethane, polyvinyl chloride, silicone or other similar materials which have good elastomeric properties. Preferably the balloon 120 is constructed of C-Flex, which is available from Consolidated Polymer Technologies, Inc. of Largo, Fla., USA. The C-Flex material allows for the formation of a balloon having very specific durometers, thereby enabling the balloon to be specifically tuned to be responsive to a pre-determined force. For example, if a pressure of one atmosphere or about 14 psi is available to be applied to a balloon and it is desirable to inflate the balloon from a first diameter of 0.90 millimeters to a second diameter of about 6 millimeters, the durometer of the C-Flex may be adjusted thereby allowing for a balloon to be formed which will expand from the first diameter to the second desired diameter in response to the applied force.

As embodied herein, specifically with reference to FIGS. 1 and 2, the balloon 120 may be radially disposed at the distal end portion 102 of the elongated body 105, wherein the balloon 120 is in fluid communication with the lumen 101 of the elongated body 105 through at least one aperture 107 formed within the wall of the elongated body 105. The aperture 107 may be formed having a generally cylindrical geometry or the aperture may be formed as an elongated slit within the wall of the elongated body 105. Furthermore, it is contemplated that the aperture 107 may be embodied having many different geometric shapes and the examples above and those which are shown in the Figures are merely exemplary.

Alternatively, the balloon 120 may be disposed asymmetrically upon only a portion of the outer wall circumference if desired. Furthermore, if desired, the proximal end of the balloon 120 may be disposed about the extreme distal end of the elongated body 105 as shown in FIG. 3, and as further depicted by U.S. Pat. No. 5,807,330, to George P. Teitelbaum, entitled "Angioplasty Catheter," the entirety of which is hereby incorporated by reference.

As shown in FIG. 3, the distal end 121 of the balloon 120 may be attached to a support member 180, wherein the support member 180 may be disposed within the lumen 101 of the elongated body 105. The support member 180 may extend beyond the distal end 121 of the balloon 120, such that the distal end 182 of the support member 180 functions in the manner as described above with reference to the flexible tip 160. Inflation of the balloon 120 as shown in FIG. 3 is accomplished through the distal end portion 102 and lumen 101 of the elongated body 105.

As embodied in FIGS. 4 and 5, the balloon 120 may be disposed about a balloon support member 140, wherein the balloon support member 140 is adapted to be received within the lumen 101 of the elongated body 105 as shown, or about the outer surface of the elongated body 105. The balloon 120 as shown in FIGS. 4 and 5 is similar to that shown and described above with reference to FIGS. 1–3, wherein like numerals designate similar features. As shown in FIGS. 4 and 5, the chamber 123 of the balloon is in fluid communication with the lumen 101 through an aperture 107' formed in the balloon support member 140, wherein the balloon support member may be constructed of the same material as that of the elongated body 105. Alternatively, the balloon support member may be constructed of any one of the materials described above with reference to the elongated body 105 and the balloon 120.

The balloon 120 may be integrally formed onto the elongated body 105 adjacent to the distal end portion 102 of the elongated body 105 through dip forming, spray forming, extrusion, heat forming, or similar manufacturing processes. Preferably the balloon 120 is formed independent of the elongated body 105 by employing one of or a plurality of the processes above and then fixedly attached to the elongated body 105. Prior to affixing the balloon 120 to the elongated body 105, any coating applied to the elongated body 105 in the area where the balloon 120 is to be affixed is first removed if necessary. The balloon 120 is then positioned adjacent the distal end portion 102 such that the proximal end 124 and the distal end 122 of the balloon 120 extend beyond the apertures 107 formed in the elongated body 105. The balloon 120 may be fixedly attached to the elongated body with a bio-compatible adhesive such as Loctite® 4014. Heat shrink tubing 125 may be disposed about the proximal end 124 and the distal end 122 of the balloon to further affix the balloon 121 to the elongated body 105.

As shown in FIGS. 2–5, a distal marker band 108 and a proximal marker band 106 may be disposed about the distal and proximal ends of the balloon 120, wherein the marker bands 106/108 may be constructed of a bio-compatible material such as stainless steel, titanium, silver, platinum, gold, radiopaque plastics, or similar materials which may be readily viewed under fluoroscopy. Preferably the marker bands 106/108 are formed of gold. The marker bands 106/108 may be separate pieces which are fixedly attached to the diameter of the elongated body utilizing mechanical methods or adhesives. Preferably, the marker bands are integrally formed upon the diameter of the elongated body through the use of spray coating, electroplating or similar methods which will deposit the marker band material upon the elongated body. It shall be understood that additional marker bands may be disposed upon the elongated body 105 at any distance along the distal portion 102.

A bio-compatible adhesive 112 may be applied to the edges of the heat shrink tubing 125 as shown in FIGS. 2–5 in order to provide a smooth transition surface between the heat shrink tubing 125 and the outer diameter of the elongated body 105. An example of a bio-compatible adhesive which may be utilize is Loctite® 3311, an ultra-violet cured adhesive.

It shall be understood that the balloon 120 may be disposed about the elongated body 105 at any distance along the distal end portion 102 of the elongated body 105, so long as the balloon is sealingly disposed in fluid communication with the lumen 101 of the elongated body 105.

As previously noted, and in accordance with the present invention the medical device also has a valve including a valve body configured to be moveably disposed at the proximal end portion of the elongated body. The valve body is movable between a closed position and an open position, wherein the valve body is configured to engage a surface of the elongated body, to seal the opening when the valve body is in the closed position.

The valve body may be configured to be movable in either an axial or radial direction. In a preferred embodiment, the valve body can be moved axially between a sealed position and an opened position, and moved radially to engage or disengage a locking mechanism disposed upon the proximal end portion of the medical device.

The valve body when in a closed position is preferably flush with the outer diameter of the elongated body 105. By providing such a low profile valve body, interventional devices may be easily passed over the medical device. In an alternative embodiment, it is contemplated that the valve body may have a diameter greater than that of the elongated body 105, so long as the outer diameter of the valve body is not so large as to inhibit the passage of interventional devices thereover.

Referring now to FIG. 9, there is shown a preferred embodiment of the valve body 150 in accordance with one aspect of the present invention. The valve body 150 includes a proximal end portion 154 and a distal end portion 152, and a cavity or/lumen 151 formed there between. The distal end portion 152 of the valve body is adapted to sealingly engage the outer diameter of the elongated body as shown in FIG. 11.

The cavity 156 of the valve body 150 may further include a pliable coating to aid in the sealing of the valve body to the elongated body 105. The coating may be silicone, urethane, TFE. In a preferred embodiment the pliable coating is a parylene coating. The valve body 150 may be constructed of a bio-compatible material such as titanium, stainless steel, polyurethane, polyvinyl chloride, Nitinol, orsimilar materials, wherein the cavity 151 of valve body is closed at proximal end portion 154 by way of a plus 158 disposed within the cavity or lumen 151 of the valve body 150.

Referring now to FIG. 10 there is shown another embodiment of the valve body 150 in accordance with the present invention. The valve body 150 shown in FIG. 10 may further include a beveled section 156, wherein the beveled section 156 may be formed at an angle β between about 0 and about 90 degrees, preferably between about 30 and about 60 degrees, more preferably the bevel 156 is formed having an angle of about 45 degrees. The bevel 156 is adapted to receive the step 117, as shown in FIG. 11, wherein the step may be formed adjacent the proximal end portion 104 of the elongated body 105, wherein the bevel 156 and step 117 form a fluid tight seal between the valve body 150 and the elongated body 105.

In accordance with the present invention, referring now to FIGS. 6, 9, and 11 there are shown partial cross-sectional side views of a first representative embodiment of the medical device 100. The proximal end portion 104 of the medical device 100 is shown in FIGS. 6, 9, and 11. FIGS. 9 and 11 illustrate a first representative embodiment of the valve body 150, wherein as shown in FIG. 11, the valve body 150 can be disposed about the proximal end portion 104 of the elongated body 105. The valve body 150 includes an elongated body having a proximal end portion 154 and a distal end portion 152, wherein the distal end portion 152 is adapted to sealingly receive the elongated body 105 of the medical device 100, and the proximal end portion has a plug 158 to close the proximate end of the value body 150. As embodied herein, the valve body 150 therefore is moved axially between an open position and a closed position as described in greater detail below.

The valve body may be constructed of any suitable bio-compatible material such as titanium, Nitinol, polymide, and other bio-compatible plastics. In a preferred embodiment the valve body is constructed of a stainless steel tube, wherein the proximal end 154 of the tube is sealed with a plug 158. The plug 158 may be constructed of a bio-compatible material such as titanium, Nitinol, stainless steel, nylon, delrin, and other similar materials. In a preferred embodiment the plug 158 is constructed of solder available from Kester of Des Plains, Ill., wherein the solder is preferably lead-free. It is further contemplated that the valve body may be constructed of a unitary body wherein the valve body may be injection molded and being constructed of plastics or metals.

The valve body 150 defines a cavity or lumen 151 therein to receive the outer diameter of the elongated body 105. If cylindrical in shape, the valve body may have an inner diameter between about 0.10 millimeters and about 2.0 millimeters, preferably between about 0.25 millimeters and about 1.0 millimeters and most preferably between about 0.300 millimeters and about 0.500 millimeters. The valve body further has a wall thickness between about 0.001 millimeters and about 0.10 millimeters, preferably between about 0.025 millimeters and about 0.05 millimeters, most preferably between about 0.03 millimeters and about 0.04 millimeters.

In accordance with the present invention, the elongated body 105 of the medical device may include a reduced cross-sectional dimension at the proximal end portion 104 to enhance sealing properties and to create a low profile valve configuration, as shown in FIGS. 6 and 11. For example, with a circular cross-sectional profile, a step 117 provides a transition between the reduced diameter area 115 and the diameter of the elongated body 105. The step 117 may be formed by grinding, molding, swaging, extruding, or other known techniques, and may be configured at any of a variety of angles, although the preferred angle α is between about 0 and about 90 degrees, preferably between about 30 and about 60 degrees and more preferably the angle is about 45 degrees. In this manner, the outer surface of the valve body is substantially flush with the outer surface of the elongated body 105 distal to the step 117. It is further contemplated that the step 117 may be formed having a convex or concave radius (not shown). That is instead of being formed as a linear transition between the two diameters, the step 117 may form a gradual radius between the two diameters, the gradual radius embodied as either convex, concave or a combination thereof.

If desired, the proximal end portion 104 of the elongated body 105 may have a closed or blind end, such as by providing a plug 103 disposed to seal the lumen 101 as shown in FIG. 6. The plug may be constructed of a biocompatible material such as titanium, stainless steel, Nitinol, delrin, nylon, or similar materials. The plug 103 embodied herein is affixed within the lumen 101 of the elongated body with a bio-compatible adhesive which will adhere to the plug 103 and the inner wall of the lumen 101. In a preferred embodiment, the plug 103 is formed of solder such as that described above with regard to the valve body 150 of FIG. 9. Alternatively, the plug 103 is not necessary because the distal end 152 of the valve body 150 sealingly contacts the outer diameter of the elongated body 105 thereby creating hemostasis within the medical device 100. It shall be understood that if the plug 103 is not disposed within the lumen 101 of the elongated body 105, the valve body 150 must include the plug 158 in order to form a fluid tight seal within the elongated body 105.

Referring now to FIGS. 11 and 12 there is shown the medical device 100 in accordance with one aspect of the present invention in use. As shown in FIG. 11, the valve body 150 is disposed upon the proximal end portion 104 of the elongated body 105, wherein the valve body is in a closed position. The distal end 152 of the valve body forms a fluid tight seal with the step 117 of the elongated body 105. The fluid tight seal may be formed through an interference fit between the distal tip 152 of the valve body and the step 117 or altertnatively, as described herein the inner diameter of the valve body may include a parylene coating for enhanced sealing properties. Referring now to FIG. 12 there is shown the valve body 150 in an open configuration. Wherein, when the valve body 150 is in an open configuration having been moved a distance away from the step 117 as denoted by the reference number 90, inflation fluid may be introduced into the lumen 101 of the elongated body 105 thereby inflating the balloon 120 of the distal tip portion 102. Inflation fluid may be introduced in a manner such as that disclosed by Teitlebaum, U.S. Pat. No. 5,807,330. Alternatively, inflation fluid may be withdrawn from the lumen 101, thereby deflating the balloon 120. As shown in FIGS. 11 and 12, the valve body 150 may be selectively opened and closed in order to control the inflation and deflation of the balloon 120. To move the valve body between an opened and closed position as shown an axial force or a radial force or a combination thereof may be applied to either or both the valve body 150 or the elongated body 105. Additionally, the valve body 150 only need be moved between about 0.005 inches and about 1.0 inches, preferably between about 0.02 inches and about 0.75 inches, most preferably between about 0.05 inches and about 0.25 inches.

Another alternative embodiment in accordance with the present invention is illustrated in FIG. 33, wherein there is shown a medical device 100 having a valve body 150 disposed upon the proximal end portion 104 of the elongated body, wherein the plug 158' of the valve body forms a fluid tight seal with the very proximal end 137 of the elongated body 105. The plug 158' may further include a pliable coating as those described above in order to effectuate a better seal with the proximal end 137 of the elongated body 105. Furthermore, frictional interference between the cavity or lumen 151 of the valve body and the Outer diameter of the elongated body 150 act to retain the valve body 150 upon the proximal end portion 104 of the elongated body 105. It shall be understood that the medical device 100 embodied and described with reference to FIG. 33 may be adapted to include any other feature described herein in relation to other embodiments of the medical device 100.

Referring now to FIGS. 7, 13–14, 18, and 19 there is shown an alternative representative embodiment of the reduced diameter area according to the present invention. As shown in FIGS. 7, 13–14, 18, and 19, the reduced diameter area may include a plurality of steps, wherein the first step 117 transitions the outer diameter of the elongated body 105 to a first reduced diameter section 115 as described above. A second step 118 may be disposed proximal to the first step 117, wherein the second step 118 provides a transition between the first reduced diameter portion 115 and a second reduced diameter portion 116.

The second step 118 may be formed at an angle between about 0 and about 90 degrees, preferably between about 30 and about 60 degrees, more preferably between about 40 and about 50 degrees.

As shown in FIGS. 13 and 14, there second step 118 can provide improved inflation and deflation of the balloon when the valve sleeve 150 is moved proximally into an opened position. This is because, as the valve body is moved from a closed position to an opened position, the valve body 150 does not have to be moved past the openings 113 formed in the wall of the elongated body 105. That is, once the distal end 152 of the valve body 150 passes proximal the second step 118 as shown in FIG. 14, a fluid flow path is formed between the second reduced diameter portion and the cavity or lumen 151 of the valve body 150. Indeed, by providing such a flow path, the extreme proximal end of the elongated body as shown in FIGS. 13 and 14, can be used to define an opening for inflation of the balloon such that additional openings need not be provided in the wall of the elongated body 105.

Referring now to FIGS. 8 and 15 there is shown yet another alternative embodiment of the proximal end portion 104 of the medical device 100 in accordance with the present invention. As shown in FIGS. 8 and 15, the proximal end portion 104 of the medical device 100 may include tapered section 515, which can be formed by known techniques, such as grinding, milling, EDM, laser cutting or swagging. The embodiment herein defines a constant angle of between about 0 and about 45 degrees, more preferably between about 0.5 and about 3 degrees. As shown in FIG. 15 a valve body 150 is disposed about the tapered section 515, wherein the distal end 152 of the valve body contacts the outer surface of the elongated body 105 thereby sealing the openings 113 when in a closed position. The valve body 150 may be moved axially, whereby an annular space is created about the distal ed 152 of the valve body 150 and the tapering outer diameter of the elongated body 105, thereby allowing for fluid to flow from the annular space into the lumen 101 and the chamber 123 FIG. 4 of the balloon.

In accordance with the present invention an opening is provided at the proximal end portion 104 of the elongated body 105, the opening being in fluid communication with the balloon 120 via the lumen 101 of the elongated body 105, wherein the opening may be embodied in a variety of configurations. As previously noted, the opening may be defined as the extreme proximal end of the elongated body. Alternatively, and as embodied herein, the opening may include at least one opening 113 disposed through the wall of the elongated body 105 at the proximal end portion 104 thereof. Preferably, and when the proximal end portion 104 is provided with an area of reduced cross-section, the opening is located within the reduced diameter area 115 or 515 of the proximal end portion 104 of the elongated body 105.

In accordance with the present invention, the opening 113 may be formed in a variety of manners, some of which are illustrated in FIGS. 6–8, and 11–32. As shown in FIGS. 6–8 and 11–32, a plurality of openings may be formed through the wall of the reduced diameter sections 115 and 116, wherein the openings are disposed along the proximal end portion 104 of the elongated body 105. The openings 113 may be formed within the wall of the elongated body utilizing manufacturing processes such as laser drilling, EDM, drilling, milling, electrochemical milling, and other similar procedures that will produce an opening through the wall of the elongated body 105.

Referring now to FIGS. 16 and 18, there is shown a first alternative embodiment of the opening 213 in accordance with the present invention, wherein like numerals denote similar features as described above with reference to the medical device 100 of the present invention. The opening 213 may be embodied in the form of at least one axially extending slit formed within the wall of the reduced diameter portion 115 or second reduced diameter portion 116.

Referring now to FIGS. 17, 19, and 29 there is shown a second alternative embodiment of the opening 313 in accordance with the present invention. The opening 313 may be embodied as a skive within the wall of the reduce diameter portion 115 or second reduced diameter portion 116. The skive may be formed within the wall of the elongated body 105 by passing a grinding wheel over the portion of the elongated body where the skive 313 is to be formed.

In accordance with the invention, there are provided additional alternative embodiments in accordance with the medical device of the present invention. As previously discussed, the medical device includes a proximal end portion and a valve body disposed thereon, wherein the valve body is movable between an open position and a closed position, in a closed position the valve body sealingly engages the outer wall of the elongated body. In an open position the valve body allows for the inflation or deflation of the balloon as previously discussed.

Referring now to FIG. 24, the elongated body 105 and the valve body 450 includes each of the elements described above and illustrated in FIG. 11. Additionally, the elongated body 105 includes a slot 413 formed within the wall of the elongated body 105 wherein the slot 413 may be formed partially into the outer wall, such as by a groove or dimple, or extend entirely through the wall of the elongated body 105 as an opening. The valve body 450 is disposed about the proximal end portion 104 of the elongated body 105 in the manner as described above. The valve body 450 may further include a protrusion 455 extending into the cavity 451 of the valve body. The protrusion 455 is slidably received within the slot 413 of the elongated body 105. The protrusion 455 therefore may retain the valve body 450 upon the proximal end 104 of the elongated body 105, and limit the proximal movement of the valve body. The protrusion 455 also may further provide tactile feedback to a user indicating whether the valve body is in an opened or closed configuration. The protrusion may be formed as a separate body attached to the valve body 450, or the protrusion may be formed integral with the valve body 450. Alternatively, the reduced diameter section may include a protrusion, either integrally formed therewith or fixedly attached thereto and the valve body may include a slot or groove adapted to receive the protrusion of the reduced diameter section.

Referring now to FIGS. 20–22, there is shown an alternative embodiment of the valve body 550 and reduced diameter portion 515. The reduced diameter portion 515 further includes a groove 519, formed in the wall of the elongated body 105. The groove 519 may be formed in the wall of the elongated body by machining, grinding, EDM milling, or similar manufacturing processes. Alternatively, the groove 519 may be formed by deforming the wall of the elongated body as shown in FIG. 30. The valve body 550 includes a pin 555 or similar protrusion extending into the cavity 551. When the valve body 550 is disposed about the reduce diameter portion 515, the pin 555 is received within the groove 519, wherein the groove 519 guides the pin 555 during translation of the valve body 550 between an opened position and a closed position. The groove 519 may be axially aligned with the lumen 101 of the elongated body 105 as shown in FIGS. 20–22, or extend helically to induce rotational movement of the valve body during displacement. Alternatively, the groove 519' may be both axially and radially aligned with the lumen 101 of the elongated body 105 as shown in FIG. 23. By having a groove 519' that is both axially and radially aligned requires that the valve body 550 be rotationally translated first and then axially translated in order to open the seal between the valve body and the elongated body. This greatly reduces or eliminates the possibility of the valve body 550 from being accidentally opened.

Referring now to FIGS. 25–27 there is shown another alternative embodiment in accordance with the medical device of the present invention. Referring now to FIG. 25 there is shown a partial cross-sectional side view of an alternative embodiment of the proximal end portion 904 of an elongated body 905, wherein the proximal end portion 904 further includes a pin 990 disposed axially through the walls and lumen 901 of the proximal end portion 904. Better understanding of the location of the pin 990 may be understood with reference to the cross-sectional top view of FIG. 26 illustrating the pin 990 being disposed through the proximal end portion 904 of the elongated body 905 perpendicular to the top view. Referring now to FIG. 27, there is shown a corresponding embodiment of a valve body 950, wherein the valve body 950 includes a track 930. The track provides a guide for positioning the valve body 950 when the groove 930 engages the pin 990. A step 917 forms a tapered portion on the proximal end of the valve body 950, wherein then the valve body 990 is inserted within the lumen 901 of the elongated body 905 the tapered portion engages the inner diameter of the proximal end portion of the elongated body therefore forming a fluid tight seal. In order to effectuate a seal between the tapered portion of the valve body 950 and the lumen 901 of the proximal end portion 904 of the elongated body 905 involves two movements, one axial movement and a second rotational force. The second rotational force requires that a deliberate action on the part of an operator to disengage the seal once the seal has been formed. The second action of the rotational force also makes it more difficult for the operator to inadvertently open the port by merely pulling axially on the valve body 950. Alternatively, the pin 990 can extend beyond the outer surface of the elongated body, and the valve body can be configured to be disposed about the outside of the proximal end portion of the elongated body with the groove being formed on an inside surface of the valve body.

The track 930 may be formed within the outer surface of the valve body 950 utilizing any of the processes as described above.

Referring now to FIGS. 28–32, there is shown an additional alternative embodiment in accordance with the present invention. Referring to FIG. 28 there is shown partial cross-sectional top view of a medical device 800, wherein the medical device 800 includes an elongated body 805 having a distal portion (not shown) and a proximal end portion 804, wherein the proximal end portion 804 includes at least one groove 830 formed therein as shown in FIG. 30. The medical device 800 further includes an opening 815 disposed adjacent to the proximal end portion 804 of the elongated body 805. As shown in FIG. 29, the opening 815 may be formed as a skive. Although the opening 815 is shown to be embodied as a skive this should not be considered limiting in any manner, it is contemplated that any of the openings described herein may be utilized in addition to or as an alternative to the skive. The skive 815 may be formed utilizing any of the methods described above.

Referring now to FIG. 31 there is shown a valve body 850, wherein the valve body includes a proximal end portion 854 and a distal end portion 852 and a tapered portion 817 disposed therebetween.

As shown in FIGS. 28 and 32, the valve body 850 is disposed proximally within the lumen 801 of the medical device 800 when in the opened position, To close the medical device, the valve body 850 is advanced distally within the lumen 801 of the elongated body 805 until the tapered section 817 passes the distal portion of the opening 815 and engages the inner surface of the proximal end portion of the elongated member. If desired, a groove and protrusion configuration also can be provided. In this manner, the valve body 850 is then rotated to lock the valve body 850 into place. Therefore, as described above with regard to FIGS. 25–27 the valve body cannot be inadvertently removed from the inner lumen 801 of the elongated body 805 without first applying a rotational force to the valve body 850.

The alternative embodiments of the medical device 900 and 800 illustrated in FIGS. 25–32 may be constructed according to the aspects and methods described above wherein the same materials may also be utilized. In addition, the valve bodies 950 and 850 may further include a coating such as that described above with regard to FIGS. 9 and 10 and the valve body 150 disclosed therein to effectuate a better seal upon the medical device 900 and 800.

The groove 830 formed within the proximal end portion 804 of the elongated body 805 may be formed utilizing any of the methods described above with reference to the medical device 100. Preferably the groove 830 is formed within the side wall of the elongated body through a crimping or dimpling process.

The medical device 100 descried and illustrated herein may be utilized in vascular interventional procedures such as angioplasty or stenting. In such procedures, an access site to the patient's vasculature is formed, typically within the patient's femoral artery. The patient is systematically heparinized during the procedure. Via the femoral artery approach, a long 9-French access sheath is inserted through the common femoral artery and is advanced into a desired position. Once access has been established, the medical device 100 is inserted into the patient's vasculature.

Through the use of fluoroscopy and the soft steerable flexible tip 160 of the medical device 100, the medical device 100 is placed adjacent a site in which a medical procedure is to be performed. Placement of the medical device 100 can be confirmed by fluoroscopy confirmation of the plurality of marker bands 108/106 disposed upon the distal end portion 102 of the medical device 100. The balloon 120 may then be inflated by opening the valve body 150, wherein inflation fluid may be introduced through the openings 113 in the proximal end portion of the medical device 100, such as described by Teitelbaum, U.S. Pat. No. 5,807,330. After the balloon 120 is inflated to a sufficient diameter, the valve body 150 may be moved into a closed position thereby forming a fluid tight seal. The balloon 120 remains inflated, while the source of inflation fluid may then be removed from the proximal end portion 104 of the medical device 100. An example of a device which may be utilized to introduce inflation fluid is a Tuohy-Borst device, wherein the Tuohy-Borst device may be removed from the medical device 100 as desired. Alternatively, a removable inflator box may be provided, which is capable of creating a sealed chamber about the proximal end portion of the elongated member, and allowing selective movement of the valve body between the open and closed positions as known in the art. Examples of inflation fluid which may be utilized are saline or carbon dioxide, preferably contrast fluid is utilized as the inflation fluid thereby enabling visualization of the balloon 120 under fluoroscopy.

At this point a balloon angioplasty catheter may be inserted over the medical device 100, wherein the balloon 120 acts to anchor the medical device 100 within the patient's vasculature as well as to occlude the vessel. If desired, the medical device 100 may be utilized to pre-dilate the stenosis within the vessel is the appropriate balloon construction is provided. Alternatively, an angioplasty balloon catheter, and/or a stent delivery device and/or other known interventional devices may be advanced over the medical device 100 to the site to perform a desired procedure as is known in the art. Debris thus created by the interventional device during an interventional procedure can be removed through an aspiration catheter which may be advanced over the medical device 100 as described below.

Following the interventional procedure, the interventional device is removed from the medical device 100 and an aspiration catheter may be advanced over the medical device 100 to a position near the site. Vigorous flushing of the site may be performed by injecting a large volume of saline into the site. Alternatively or additionally, debris may be removed distal the lesion through a lumen of an aspiration catheter by selectively positioning the aspiration catheter within the site.

After debris has been removed from the site and the aspiration catheter is removed from the medical device 100, the valve body 150 is moved from a closed position to an open position wherein the inflation fluid may be removed, thereby deflating the balloon 120 of the medical device 100. At this time the medical device 100 may be withdrawn from the patient's vasculature. Alternatively, the medical device 100 may remain as positioned, wherein additional interventional procedures may be performed at the site, wherein the site may be aspirated as described following any interventional procedure. The medical device 100 may remain as positioned as long as there is a need to perform additional interventional procedures.

Although the present invention has been described in considerable detail with reference to certain preferred embodiments, it is contemplated that one skilled in the art may make modifications to the device herein without departing from the scope of the invention. Therefore, the scope of the amended claims should not be considered limited to the embodiments described herein.

What is claimed is:

1. A medical device for vessel occlusion, the medical device comprising:
    an elongated body having a distal end portion, a proximal end portion, and a lumen disposed therethrough, at least part of the proximal end portion of the elongated body having an outer cross-sectional dimension less than an outer cross-sectional dimension of another portion of the proximal end portion of the elongated body;
    a balloon disposed at the distal end portion of the elongated body, the balloon in fluid communication with the lumen;
    an opening defined at the proximal end portion of the elongated body, the opening being in fluid communication with the balloon via the lumen; and
    a valve body moveably disposed at the proximal end portion of the elongated body, the valve body movable between a closed position and an open position, the valve body configured to engage an exterior surface of the proximal end portion of the elongated body, distal to the opening, to seal the opening when the valve body is in the closed position.

2. The medical device according to claim 1, wherein the surface engaged by the valve body when in the closed position is an outer surface of the elongated body.

3. The medical device according to claim 1, wherein at least part of the proximal end portion of the elongated body has an outer cross-sectional dimension less than an outer cross-sectional dimension of the distal end portion of the elongated body.

4. The medical device according to claim 3, wherein the valve body includes a side wall having a cavity defined therein to receive the proximal end portion of the elongated body, the valve body having an outer surface substantially flush with an outer surface of the distal end portion of the elongated body when in the closed position.

5. The medical device according to claim 1, wherein the opening is defined in a side wall of the proximal end portion of the elongated body.

6. The medical device according to claim 1, wherein an inflation port is defined in a side wall of the valve body.

7. The medical device according to claim 1, wherein the valve body and the elongated body are configured for mating engagement to prevent inadvertent movement of the valve body at least when in the closed position.

8. The medical device according to claim 7, wherein the mating engagement includes a projection extending from a surface of at least one of the valve body and elongated body.

9. The medical device according to claim 1, wherein the valve body is moveable in an axial and rotational direction relative to the elongated body.

10. A medical device for vessel occlusion, the medical device comprising:
    an elongated body having a distal end portion, a proximal end portion, and a lumen disposed therethrough, at least part of the proximal end portion of the elongated body having an outer cross-sectional dimension less than an outer cross-sectional dimension of another portion of the proximal end portion of the elongated body;
    a balloon disposed at the distal end portion of the elongated body, the balloon in fluid communication with the lumen;
    an opening defined at the proximal end portion of the elongated body, the opening being in fluid communication with the balloon via the lumen; and
    a valve body moveably disposed at the proximal end portion of the elongated body, the valve body movable between a closed position and an open position, the valve body configured to engage an outer surface of the elongated body to seal the opening when the valve body is in the closed position.

11. The medical device according to claim 10, wherein at least part of the proximal end portion of the elongated body has an outer cross-sectional dimension less than an outer cross-sectional dimension of the distal end portion of the elongated body.

12. The medical device according to claim 11, wherein the valve body includes a side wall having a cavity defined therein to receive the proximal end portion of the elongated body, the valve body having an outer surface substantially flush with an outer surface of the distal end portion of the elongated body when in the closed position.

13. The medical device according to claim 10, wherein the valve body and the elongated body are configured for mating engagement to prevent inadvertent movement of the valve body at least when in the closed position.

14. The medical device according to claim 13, wherein the mating engagement includes a projection extending from a surface of at least one of the valve body and elongated body.

15. The medical device according to claim 10, wherein the valve body is moveable in an axial and rotational direction relative to the elongated body.

16. The medical device according to claim 10, wherein the elongated body is constructed of Nitinol.

17. The medical device according to claim 10, wherein the proximal end of the elongated body has a diameter less than the distal end.

18. The medical device according to claim 17, wherein the elongated body further includes a step adjacent to the proximal end of the elongated body wherein the step transitions the elongated body between the distal diameter and the proximal diameter.

19. The medical device according to claim 18, wherein when the valve body is in a closed position the valve body sealingly engages the step.

* * * * *